US012167905B2

(12) United States Patent
Gomez et al.

(10) Patent No.: US 12,167,905 B2
(45) Date of Patent: *Dec. 17, 2024

(54) METHODS AND SYSTEM FOR HEMORRHAGE-SPECIFIC DETERMINATIONS

(71) Applicant: CERNER INNOVATION, INC., Kansas City, KS (US)

(72) Inventors: Patrizia Smouse Gomez, Kansas City, MO (US); Jessica Alford, Peculiar, MO (US); Krystal Cunningham, Kansas City, MO (US); Ginger Querner, Lee's Summit, MO (US); Justin Peterson, Olathe, KS (US); Yash Goyal, Overland Park, KS (US); Hemin Merchant, Overland Park, KS (US); Peng Li, Kansas City, MO (US); Amy Stafford, Kansas City, MO (US)

(73) Assignee: Cerner Innovation, Inc., Kansas City, MO (US)

(*) Notice: Subject to any disclaimer, the term of this patent is extended or adjusted under 35 U.S.C. 154(b) by 490 days.

This patent is subject to a terminal disclaimer.

(21) Appl. No.: 17/508,541

(22) Filed: Oct. 22, 2021

(65) Prior Publication Data

US 2022/0039672 A1 Feb. 10, 2022

Related U.S. Application Data

(63) Continuation of application No. 14/980,799, filed on Dec. 28, 2015, now Pat. No. 11,185,236.

(51) Int. Cl.
*A61B 5/02* (2006.01)
*G01G 19/00* (2006.01)
(Continued)

(52) U.S. Cl.
CPC ......... *A61B 5/02042* (2013.01); *G01G 19/00* (2013.01); *G16H 10/60* (2018.01);
(Continued)

(58) Field of Classification Search
CPC ....... A61B 5/02042; A61B 5/01; A61B 5/021; A61B 5/024; A61B 5/0816; A61B 5/4343;
(Continued)

(56) References Cited

U.S. PATENT DOCUMENTS

| 4,562,842 A | 1/1986 | Morfeld et al. |
| 4,922,922 A | 5/1990 | Pollock et al. |

(Continued)

FOREIGN PATENT DOCUMENTS

CN 103617346 B 5/2017

OTHER PUBLICATIONS

Prata et al., "Measurement of Postpartum Blood Loss", BMJ 2010;340:c555, Available online at: , Feb. 1, 2010, 3 pages. (Year: 2010).*
Shields et al., "Comprehensive Maternal Hemorrhage Protocols Improve Patient Safety and Reduce Utilization of blood Products", American Journal of Obstetrics and Gynecology, vol. 205, Issue 4, Oct. 1, 2011, 8 pages. (Year: 2011).*
(Continued)

*Primary Examiner* — Joshua B Blanchette
(74) *Attorney, Agent, or Firm* — Kilpatrick Townsend & Stockton LLP

(57) ABSTRACT

Methods and a system are provided for assessing postpartum hemorrhage risk and postpartum hemorrhage stages in a clinical setting. Generally, a clinician may indicate that the mass of several bloody items, indicated in type and quantity, is to be measured using a scale. The mass of bloody items is compared to the known unused dry mass of such items in
(Continued)

order to accurately determine the quantitative blood loss (QBL) of a patient at the bedside. The cumulative QBL can be updated by weighing additional items. Based on the cumulative QBL, the patient's vital signs, and other factors, a corresponding hemorrhage stage is identified and communicated to the clinician. Recommendations specific to the hemorrhage stage are provided to a clinician. Some recommendations are selectable actions that trigger automatic placement of medical orders and notifications to relevant medical services, such as a blood bank or anesthesia.

20 Claims, 14 Drawing Sheets

(51) Int. Cl.
*G16H 10/60* (2018.01)
*G16H 50/30* (2018.01)
*A61B 5/00* (2006.01)
*A61B 5/01* (2006.01)
*A61B 5/021* (2006.01)
*A61B 5/024* (2006.01)
*A61B 5/08* (2006.01)

(52) U.S. Cl.
CPC .............. *G16H 50/30* (2018.01); *A61B 5/01* (2013.01); *A61B 5/021* (2013.01); *A61B 5/024* (2013.01); *A61B 5/0816* (2013.01); *A61B 5/4343* (2013.01)

(58) Field of Classification Search
CPC ........ G01G 19/00; G01G 19/44; G16H 10/60; G16H 50/30
See application file for complete search history.

(56) References Cited

U.S. PATENT DOCUMENTS

| | | | |
|---|---|---|---|
| 5,009,275 | A | 4/1991 | Sheehan |
| 8,784,313 | B2 | 7/2014 | Mebazaa et al. |
| 2008/0221396 | A1* | 9/2008 | Garces ............... A61M 1/0286 |
| | | | 600/300 |
| 2008/0243547 | A1 | 10/2008 | Brett et al. |
| 2009/0094063 | A1 | 4/2009 | Ennett |
| 2013/0303870 | A1* | 11/2013 | Satish ................. A61B 5/4848 |
| | | | 600/371 |
| 2015/0025329 | A1 | 1/2015 | Amarasingham et al. |
| 2015/0168207 | A1* | 6/2015 | Pollock .................. A61B 5/208 |
| | | | 177/1 |
| 2017/0185739 | A1 | 6/2017 | Gomez et al. |
| 2017/0351894 | A1 | 12/2017 | Satish et al. |

OTHER PUBLICATIONS

Barbieri, Robert L., "Planning reduces the risk of maternal death. This tool helps", OBG Management vol. 21 No.8, Aug. 2009, 3 pages.

Ob Hem Task FORCE, "Appendix A: Stage of Hemorrhage Poster for Cart", California Maternal Quality Care Collaborations, Mar. 24, 2015, pp. 156-158.

Prata et al., "Measurement of Postpartum Blood Loss", BMJ 2010;340:c555, Available online at: <https://pubmed.ncbi.nlm.nih.gov/20123836/>, Feb. 1, 2010, 3 pages.

Shields et al., "Comprehensive Maternal Hemorrhage Protocols Improve Patient Safety and Reduce Utilization of Blood Products", American Journal of Obstetrics and Gynecology, vol. 205, Issue 4, Oct. 1, 2011, 8 pages.

* cited by examiner

METHODS AND SYSTEM FOR HEMORRHAGE-SPECIFIC DETERMINATIONS

CROSS REFERENCE TO RELATED APPLICATION

This is patent application is a continuation that claims the benefit of and priority to U.S. application Ser. No. 14/980,799, filed on Dec. 28, 2015 and entitled "Methods and System for Hemorrhage-Specific Determinations", which is incorporated by reference herein, in its entirety.

BACKGROUND

Emerging use of technology and devices has previously failed to address the difficulties of assessing a patient's risk for an occurrence of postpartum hemorrhage prior to labor and delivery, and accurately determining a patient's quantitative blood loss during postpartum hemorrhage. More particularly, when a clinician is faced with a postpartum hemorrhage emergency, the clinician must manually estimate a patient's blood loss based on visual assessments and past experiences with postpartum hemorrhage, in a very limited amount of time. Manual calculation is error prone as the eyes alone cannot accurately quantify blood loss, any visual inspection of a gynecological bleed is limited, and a bedside physical examination (i.e., using of the hands to locate) of a gynecological bleed is the most accessible way to assess the postpartum hemorrhage before surgical intervention (e.g., in an operating room) is needed. Because manual determination of blood loss is inaccurate, a patient's safety, care, and outcome may be negatively impacted. Although at least some of these problems are apparent, an effective solution has not been proposed or implemented, as set forth hereinafter.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The present invention is defined by the claims.

In brief and at a high level, this disclosure describes, among other things, methods, systems, and computer-readable media for making hemorrhage-specific determinations. Generally, during a postpartum hemorrhage event, a quantitative blood loss of a patient is determined and updated based on items exposed to the patient's blood, whether minimally or saturated therewith. In embodiments presented herein, the quantitative blood loss is assessed based on the known dry weights of typical or standard items used by clinicians. Based on the quantitative blood loss, the patient's vital signs, lab results, and/or patient medical history, a postpartum hemorrhage stage can be identified and updated throughout the postpartum hemorrhage event. Once the postpartum hemorrhage stage is identified, recommendations are provided to a clinician and his/her medical team automatically so the clinician can quickly make treatment and intervention decisions to reduce and stop the postpartum hemorrhage. Furthermore, clinicians can select actionable recommendations to automatically send notifications to other medical services regarding the postpartum hemorrhage event as well as place medical orders.

The claimed methods, systems, and computer-readable media of the present application represent a Postpartum Hemorrhage Advisor. Not only does the claimed invention provide clinicians recommendations for intervention during a patient's postpartum hemorrhage event, but the Advisor provides for modifying the patient's electronic medical record (EMR) during a postpartum hemorrhage event that is efficient, reduces human error, user friendly, and cost-effective. Users of EMRs or electronic health records (EHR) utilizing the claimed invention will notice improved performance of an EMR, an EMR database, and will receive recommendations for patient care and intervention during a postpartum hemorrhage event. Furthermore, the Advisory reduces the number of "clicks" or entries a computer user has to make in an EMR or HER which results in reducing memory utilization, CPU cycles, the number of operations that need to be performed by the computer, and power consumption. The resulting cost savings and operational efficiencies of a computer EMR magnify the potential benefits of this technology.

BRIEF DESCRIPTION OF THE DRAWINGS

Embodiments are described in detail below with reference to the attached drawing figures, wherein:

FIG. 6 is an exemplary GUI for assessing postpartum hemorrhage in accordance with an embodiment of the present invention;

FIG. 7 is an exemplary GUI for assessing postpartum hemorrhage in accordance with an embodiment of the present invention;

FIG. 8 is an exemplary GUI for assessing postpartum hemorrhage in accordance with an embodiment of the present invention;

FIG. 9 is an exemplary GUI for assessing postpartum hemorrhage in accordance with an embodiment of the present invention;

FIG. 10 is an exemplary GUI for assessing postpartum hemorrhage in accordance with an embodiment of the present invention;

FIG. 11 is an exemplary GUI for assessing postpartum hemorrhage in accordance with an embodiment of the present invention;

FIG. 12 is an exemplary GUI for assessing postpartum hemorrhage in accordance with an embodiment of the present invention;

FIG. 13 is an exemplary GUI for assessing postpartum hemorrhage in accordance with an embodiment of the present invention; and FIG. 14 is an exemplary GUI for assessing postpartum hemorrhage in accordance with an embodiment of the present invention.

DETAILED DESCRIPTION

Figure 1:
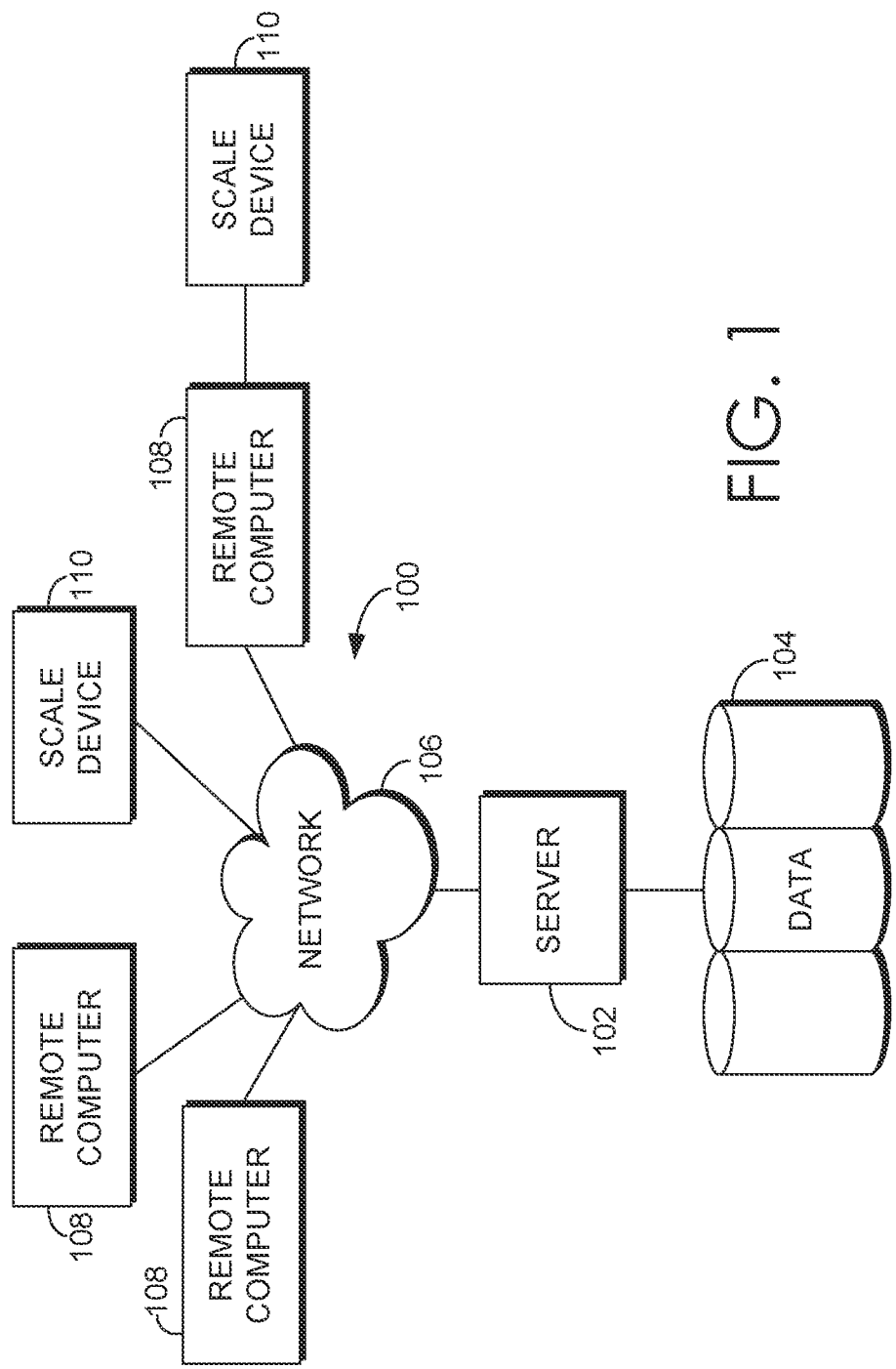
FIG. 1 is a block diagram of an exemplary computing system suitable to implement embodiments of the present invention.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described. In the same vein, the claimed subject matter might also be embodied in other ways, to include different components or combinations of components, similar to those described in this document, in conjunction with other present or future technologies.

As will be described, methods and a system for accurately assessing and tracking blood loss during hemorrhage as well as determining postpartum hemorrhage-specific stages are provided. In the clinical setting, it is difficult for an experienced clinician to predict when a patient is at risk for postpartum hemorrhage, to quantify actual blood loss during hemorrhage, and assess which clinical actions to implement that are responsive to the hemorrhage (e.g., stop or reduce blood loss) and appropriate for quantitative blood loss (e.g., a hemorrhage stage), especially when the source or location of the postpartum hemorrhage is difficult to locate. By improving the clinician's ability to predict postpartum hemorrhage risk in particular patients, preventative clinical measures can be implemented to reduce negative outcomes for the patient and increase responsive times to actual instances of postpartum hemorrhage. For example, a hemorrhage cart may be moved to the room of a patient having increased risk of postpartum hemorrhage during labor and delivery prior to any hemorrhage occurrence. In another example, a blood bank may be notified in advance that a patient having a high risk for postpartum hemorrhage has been admitted for labor and deliver and the patient's blood type is B negative. In yet another example, special staff members may be called to the patient room of a patient at risk for postpartum hemorrhage during labor and delivery, and/or a specific service (e.g., anesthesia) may be notified to be ready or "on call" when a patient at risk for postpartum hemorrhage is admitted to the hospital.

In addition to providing advance notice of postpartum hemorrhage risk, the invention provides methods and systems that facilitate accurate measurements of actual blood loss and provide postpartum hemorrhage stage specific interventions for clinician evaluation in an on-going fashion during an actual postpartum hemorrhage event. Upon a postpartum hemorrhage event occurring for a patient, for example, the clinician and medical staff utilize a computing device and a scale device to assess and monitor the quantitative blood loss of the patient, without the need to rely on faulty and inaccurate visual estimations. During the postpartum hemorrhage event, items may become wet with blood and/or saturated with blood as the items are used to absorb blood, aid coagulation, and apply pressure, for example. These used items are weighed using the scale in light of the items' previously known dry weight, so that the computing device may accurately determine a patient's quantitative blood loss. The clinicians and medical staff may input the type and quantity of used items into the computing device and/or the scale. Using the quantitative blood loss as well as other factors that will be discussed hereinafter, the computing device determines an accurate postpartum hemorrhage stage to the clinician, regarding the patient's status.

The computing device also provides the clinician with interventions that the clinician may perform or orders to place that are based on the postpartum hemorrhage stage, the patient's medical history, and other factors. The clinician may evaluate the patient's blood loss throughout the postpartum hemorrhage event and the computing device may dynamically provide up-to-date quantitative blood loss information, postpartum hemorrhage stage information, and clinical intervention recommendations based on the quantitative blood loss information, postpartum hemorrhage stage information, and user input from a clinician and/or medical staff.

The computing device may provide interventions that are selected by user input (e.g., touchscreen buttons) for actionable items. Exemplary actionable items are items that prompt a user to perform a specific action. The performance of an actionable item may be noted or logged in a single user input (e.g., one click of mouse, single gesture received via a user interface, a particular keystroke or combination of keystrokes concurrently or in sequence) in some embodiments. For example, an actionable item may be displayed to a user, so that the user can touch a touchscreen to place an order for six units of fresh frozen plasma (FFP), to place an order for two unit of platelets, to send a notification to the operating room (OR) team to prepare immediately for surgery, to communicate a notification to the blood bank that a massive blood transfusion is needed, to record all user input and patient monitoring device information into an EMR of the patient, an EHR, and the like, for example. In this way, the actionable item may be performed. Actionable items are generally communicated to be user selectable such that selection results in the performance of an action via the network, computing device, and/or scale, for example. In further embodiments, other actionable items might foreseeably include a user voice command received by the computing device and processed therein, wherein the voice command indicates that an actionable item (regarding a recommendation) is to be performed in response to the voice command, for example, automatically recording all the hemorrhage event data to an EMR and/or and EHR stored at a server along with a time stamp. Another exemplary actionable item may include receiving a user indication to automatically place a medical order, wherein the recommendation includes the specific details of the medical order. In this way, the user may simply use a mouse to click a recommendation displayed on a user interface in order to place the medical order specified in the recommendation, for example.

It will be understood and is accepted that 1000 grams (g) are equivalent to one kilogram (kG), and 1000 milliliters (mL) are equivalent to one liter (L). Further, it will be understood by one skilled in the art that approximately one mL of human blood has a corresponding mass of one gram. Therefore, 1000 mL of human blood could also be reported as 1000 g, 1 kG, or one L of human blood. As used herein, the term "blood" will generally refer to human blood. It will also be understood that, as used herein, blood or human blood includes platelets, proteins, red blood cells, plasma, water, other biologic components, and/or any pharmaceutical additives as would be understood and known by those skilled in the art. Further, it will be understood that the above statement that one gram generally corresponds to one mL of blood is an approximation, as the exact composition of blood of an individual human patient may be unique and slight variations are likely to exist naturally, due to medications, genetic, and/or epigenetic factors. Further, exact blood composition, and the respective weight and mass thereof, may be affected by medication (e.g., anticoagulants, blood thinners), diseases, or conditions (e.g., sickle cell disease, anemia, bone marrow disorder).

Previously, clinicians and medical staff were forced to rely on their previous experiences regarding hemorrhage events and visual acuity to estimate blood loss during a postpartum hemorrhage event. In the case of postpartum hemorrhage, blood loss may be especially difficult to accurately assess because visual inspection of an item fails to reveal exactly how much blood may or may not have been absorbed by the item. Additionally, locating the hemorrhage source is difficult and invasive, making it difficult to estimates the rate of blood loss. As will be understood, postpartum hemorrhage events are a true emergency and a potentially life-threatening situation that requires fast intervention and even faster decision making by the clinician and medical team. Without the ability to accurately determine a patient's blood loss, a clinician and medical team have to make intervention decisions with the limited information available (e.g., visuals). Further, the inaccuracies of blood loss estimation based on visuals and clinician experience are compounded by the fact that a pregnant patient carries upwards of 10 liters of blood, in comparison to a non-pregnant patient having on average 5 liters of blood, which may make it difficult for clinicians and medical staff to compare a postpartum hemorrhage with other hemorrhage experiences.

The problem of quickly and accurately assessing blood loss, tracking blood loss of a patient during acute hemorrhaging (e.g., postpartum hemorrhage) or management of blood loss in a controlled clinical setting (e.g., surgical procedures), and accessing diagnostic recommendations specific to the blood loss are all addressed by the present invention.

In a first embodiment, a system for assessing postpartum hemorrhage risk is provided. In embodiments, the system includes a computer server that stores information for a plurality of patients including a first patient, a scale configured to measure mass of one or more items; and a computing device in a healthcare information system. In the system, the computing device is communicatively coupled to the scale and is programmed to receive an indication from a clinician-user to measure one or more items via the scale communicatively coupled to the computing device. The computing device is further programmed to reference information stored on the computer server to identify whether one or more risk factors associated with an increase in likelihood of postpartum hemorrhage occurrence are present in information specific to the first patient. The computing device is programmed to measure a mass of the one or more items via the scale and determine a quantitative blood loss of a patient based on the mass of the one or more items, a predetermined dry mass of the one or more items, and when present, the one or more risk factors in the information specific to the first patient. In embodiments, the computing device may identify a hemorrhage stage that corresponds to the quantitative blood loss of the patient and communicate the hemorrhage stage and the quantitative blood loss of the patient to the clinician-user. And, the computing device may communicate one or more recommendations to the clinician-user, wherein the one or more recommendations are specific to the hemorrhage stage, in some embodiments. In embodiments, the hemorrhage stage and quantitative blood loss are automatically saved to an EMR of the patient.

In another embodiment, one or more computer storage media having computer-usable instructions thereon are provided. When the computer-usable instructions of the computer storage media are used by one or more computing devices, said instructions cause the one or more computing devices perform a method for postpartum hemorrhage risk assessment. In embodiments, the method is performed or executed at a computing device coupled to a scale. The method includes receiving an indication from a clinician-user to measure one or more items via the scale and receiving an indication of a weight of the one or more items measured. Then, the method includes determining a quantitative blood loss of a patient based on the indication of the weight of the one or more items, in embodiments. And, a hemorrhage stage that corresponds to the quantitative blood loss of the patient is identified. In embodiments, the hemorrhage stage and the quantitative blood loss of the patient are communicated to the clinician-user. The method includes, in embodiments, communicating one or more recommendations to the clinician-user wherein the recommendations are specific to the hemorrhage stage identified.

In yet another embodiment, a computerized method for postpartum hemorrhage risk assessment is provided. In embodiments, the method includes referencing stored patient information to identify one or more risk factors associated with an increase in likelihood of postpartum hemorrhage occurrence. The method includes receiving an indication from a clinician-user to measure one or more items via a scale device, in embodiments. Then, a weight of the one or more items is measured and a quantitative blood loss of a patient is determined. The quantitative blood loss of the patient is determined based on the weight of the one or more items and a predetermined dry weight of the one or more items. The method continues by identifying a postpartum hemorrhage stage that corresponds to the quantitative blood loss of the patient. And, the method includes communicating the postpartum hemorrhage stage and the quantitative blood loss of the patient to the clinician-user, and communicating one or more recommendations to the clinician-user, in embodiments. The one or more recommendations are specific to the postpartum hemorrhage stage.

Referring now to the drawings in general, and initially to FIG. 1 in particular, an exemplary computing system environment, for instance, a healthcare information and management system, in which embodiments of the present invention may be implemented is illustrated and designated generally as reference numeral 100. It will be understood and appreciated by those of ordinary skill in the art that the illustrated medical information computing system environment 100 is merely an example of one suitable computing environment and is not intended to suggest any limitation as to the scope of use or functionality of the invention. Neither should the healthcare information and management system be interpreted as having any dependency or requirement relating to any single component or combination of components illustrated therein.

The present invention may be operational with numerous other general-purpose or special-purpose computing system environments or configurations. Examples of well-known computing systems, environments, and/or configurations that may be suitable for use with the present invention include, by way of example only, personal computers, server computers, handheld or laptop devices, multiprocessor systems, microprocessor-based systems, set top boxes, programmable consumer electronics, network PCs, minicomputers, distributed computing environments that include any of the above-mentioned systems or devices, and the like. In embodiments, the present invention may be implemented in computing system environments employed within healthcare facilities, such as a distributed network that communicatively couples multiple, affiliated hospitals and/or related outpatient clinics. For example, computing systems employed for healthcare facility implementation may include, in addition to those examples of well-known computing systems, patient monitoring devices, scale devices, intravenous pumps, and the like.

The present invention may be described in the general context of computer-executable instructions, such as program modules, being executed by a computing device. Generally, program modules include, but are not limited to, routines, programs, objects, components, and data structures that perform particular tasks or implement particular abstract data types. The present invention may also be practiced in distributed computing environments where tasks are performed by remote processing devices that are linked through a communications network. In a distributed computing environment, program modules may be located in local and/or remote computer storage media including, by way of example only, memory storage devices.

With continued reference to FIG. 1, the exemplary healthcare information and management system includes a computing device in the form of a computer server, illustrated as server 102. The server 102 may be employed within the healthcare information and management system. Components of the server 102 may include, without limitation, a processing unit, internal system memory, and a suitable system bus for coupling various system components, including a database or database cluster. The system bus may be any of several types of bus structures, including a memory bus or memory controller, a peripheral bus, and a local bus, using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA®) local bus, and Peripheral Component Interconnect (PCI) bus, also known as Mezzanine bus.

The server 102 typically includes, or has access to, a variety of computer-readable media, for instance, a database or data store 104. Computer-readable media can be any available media that may be accessed by server 102, and includes volatile and nonvolatile media, as well as removable and non-removable media. By way of example, and not limitation, computer-readable media may include computer storage media and communication media.

Computer storage media may include, without limitation, volatile and nonvolatile media, as well as removable and non-removable media, implemented in any method or technology for storage of information, such as computer-readable instructions, data structures, program modules, or other data. In this regard, computer storage media may include, but is not limited to, RAM, ROM, EEPROM, flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by the server 102. Computer storage media does not comprise signals per se.

Communication media typically embodies computer-readable instructions, data structures, program modules, or other data in a modulated data signal, such as a carrier wave or other transport mechanism, and may include any information delivery media. As used herein, the term "modulated data signal" refers to a signal that has one or more of its attributes set or changed in such a manner as to encode information in the signal. By way of example, and not limitation, communication media includes wired media such as a wired network or direct-wired connection, and wireless media such as acoustic, RF, infrared, and other wireless media. Combinations of any of the above also may be included within the scope of computer-readable media.

The computer storage media discussed above and illustrated in FIG. 1, including a data store 104, provides storage of computer-readable instructions, data structures, program modules, and other data for the server 102. As such, the server 102 may be programmed to perform various tasks using computer-readable instructions, including embodiments of methods described hereinafter. For example, the server 102 may be programmed with one or more modules that perform methods for a postpartum hemorrhage risk assessment.

In embodiments, the server 102 is coupled to a data store 104 such that the server 102 may access, communicate with, and otherwise retrieve information stored by the data store 104. In embodiments, the data store 104 is a database configured to store information encoded as data. In some embodiments, the data store 104 is configured to permanently store data such as EMRs for a plurality of patients. In some embodiments, the data store 104 is configured to store data regarding hemorrhage risk for each of a plurality of patients. Additionally or alternatively, the data store 104 may be configured to store data regarding hemorrhage risk for groups within the plurality of patients (e.g., patient information; patient demographics such as age, race; a patient's medical history such as the number of previous births, a multiple pregnancy (i.e., twins, triplets), a blood disorder, a medication, etc.). Exemplary hemorrhage risk data may leverage the plurality of EMRs of patients and include one or more of a risk grade (e.g., A, B, C, D, F), a risk level (e.g., low risk, medium risk, high risk), and a risk score (e.g., a numerical value representing a scale, such 1 to 5, or 1 to 100). Additionally or alternatively, the data store 104 may be configured to store data including risk factors associated with an increase in likelihood of postpartum hemorrhage generally, or further, risk factors that are associated with one or more specific patients, in some embodiments. As such, the data store 104 includes memory. In another embodiment, the data store 104 is configured to temporarily store data, such that the data store 104 may act, at least partially, as a cache for faster data access and retrieval by the server 102. Additionally or alternatively, the data store 104 includes long-term permanent data storage for storing one or more EMRs of patients associated with a medical entity (e.g., hospital, group of hospitals, physicians group, and an outpatient clinic). In embodiments, the data store 104 includes computer-readable media, as previously described hereinabove. In further embodiments, the data store 104 may comprise a database that stores clinical intervention guidance and recommendations for hemorrhage events. In embodiments, the data store 104 may include thresholds for triggering the communication of each of a plurality of recommendations and/or interventions, as well as thresholds or parameters that may be used to trigger the server 102 and/or remote computing devices 108 to automatically store information regarding the postpartum hemorrhage event, recommendations, and/or interventions, for example, to one or more data files, a subset of data files, a log file, an EMR, and/or and EHR stored in the data store 104.

The server 102 may operate in a distributed network environment 106 of the healthcare information and management system 100. The server 102 and the distributed network environment 106 use logical connections to communicate with one or more remote computers 108 and/or scale devices 110. Remote computers 108 may be located at a variety of locations in a medical or research environment, for example, but not limited to, clinical laboratories, hospitals and other inpatient settings, veterinary environments, ambulatory settings, medical billing and financial offices, hospital administration settings, home healthcare environments, and clinicians' offices. Clinicians and medical staff may include, but are not limited to, a treating physician or physicians; specialists such as obstetrics and gynecology (OB/GYN) physicians, surgeons, radiologists, cardiologists, and oncologists; emergency medical technicians; physicians' assistants; nurse practitioners; nurses; nurses' aides; pharmacists; dieticians; microbiologists; laboratory experts; genetic counselors; researchers; veterinarians; students; and the like. The remote computers 108 may also be physically located in non-traditional healthcare environments so that the entire healthcare community may be capable of integration with the distributed network environment 106.

The remote computers 108 may include a portable computer, a laptop, a touchscreen device, a notepad, or a mobile device, in some embodiments. Exemplary remote computer 108 may include personal computers, servers, routers, network PCs, peer devices, other common network nodes, or the like, and may include some or all of the components described above in relation to the server 102. The devices may be personal digital assistants or other like devices, in some embodiments.

The remote computers 108 may include, incorporate, and/or be coupled to a measurement device, such as scale device 110, for measuring weight and/or mass. Throughout this disclosure, weight and mass will be used interchangeably as measurement units used by methods described herein for quantifying blood loss. In embodiments, a scale or scale device may be communicatively coupled to one or more of the remote computers 108 so that the scale can measure and communicate (e.g., wirelessly or non-wirelessly), in real-time or near real-time, weight and/or mass measurements obtained in the clinical setting to a computing device, in embodiments. The scale may be directly coupled to one or more of the exemplary remote computers 108 or alternatively may communicate with a remote computer 108 via the network environment 106. In embodiments, a computing device (e.g., remote computer 108) may utilize information or data that represents measurements obtained using the scale. The computing device may use the information and/or data to accurately and dynamically determine up-to-date quantitative blood loss of a patient, determine hemorrhage stage information, and/or provide clinical intervention recommendations based on the quantitative blood loss information, hemorrhage stage information, and user input from a clinician and/or medical staff. In further embodiments, additional patient monitoring devices (not shown) may also be coupled, directly or indirectly, to the scale and computing device so as to provide physiological information that is useful to determining quantitative blood loss, determining hemorrhage stage, and/or providing clinical intervention recommendations. For example, patient monitoring device(s) communicate to the computing device that measurements indicate the patient's blood pressure is dropping and pulse rate is increasing, as such information may be used by the computing device when determining the hemorrhage stage and/or clinical intervention recommendations, including actionable actions.

Continuing, exemplary network environment 106 may include, without limitation, local area networks (LANs) and/or wide area networks (WANs). Such networking environments are commonplace in offices, enterprise-wide computer networks, intranets, and the Internet. When utilized in a WAN networking environment, the server 102 may include a modem or other means for establishing communications over the WAN, such as the Internet. In a networked environment, program modules or portions thereof may be stored in the server 102, in the data store 104, or on any of the remote computers 108. For example, and not by way of limitation, various application programs may reside on the memory associated with any one or more of the remote computers 108. It will be appreciated by those of ordinary skill in the art that the network connections shown are exemplary and other means of establishing a communications link between the computers (e.g., server 102 and remote computers 108) may be utilized.

In embodiments, one or more of the remote computing devices 108, and/or the server 102, may be configured to perform methods, as described hereinafter. For instance, a computing device and/or the server may: access a patient's EMR and/or an EHR during a postpartum hemorrhage event; modify the patient's EMR and/or an EHR before, during, and/or after a postpartum hemorrhage event; create new data files to be stored in a patient's EMR or in association with a patient's EMR and/or an EHR; generate a subset of data files that capture information of the postpartum hemorrhage event including patient's vital signs, clinician actions taken, and recommendations presented to a user; store one or more data files to the EMR and/or an EHR, permanently and/or temporarily (e.g., to a cache); and the like. This list should not be construed as limiting as the list illustrates merely a few of the functions performed by the components of FIG. 1. The performance of such functions may be automatically triggered and/or manually triggered by user input received, in some embodiments.

Although many other internal components of the server 102 and the remote computers 108 are not shown, those of ordinary skill in the art will appreciate that such components and their interconnection are well known. Accordingly, additional details concerning the internal construction of the server 102 and the remote computers 108 are not further disclosed herein.

Figure 2:
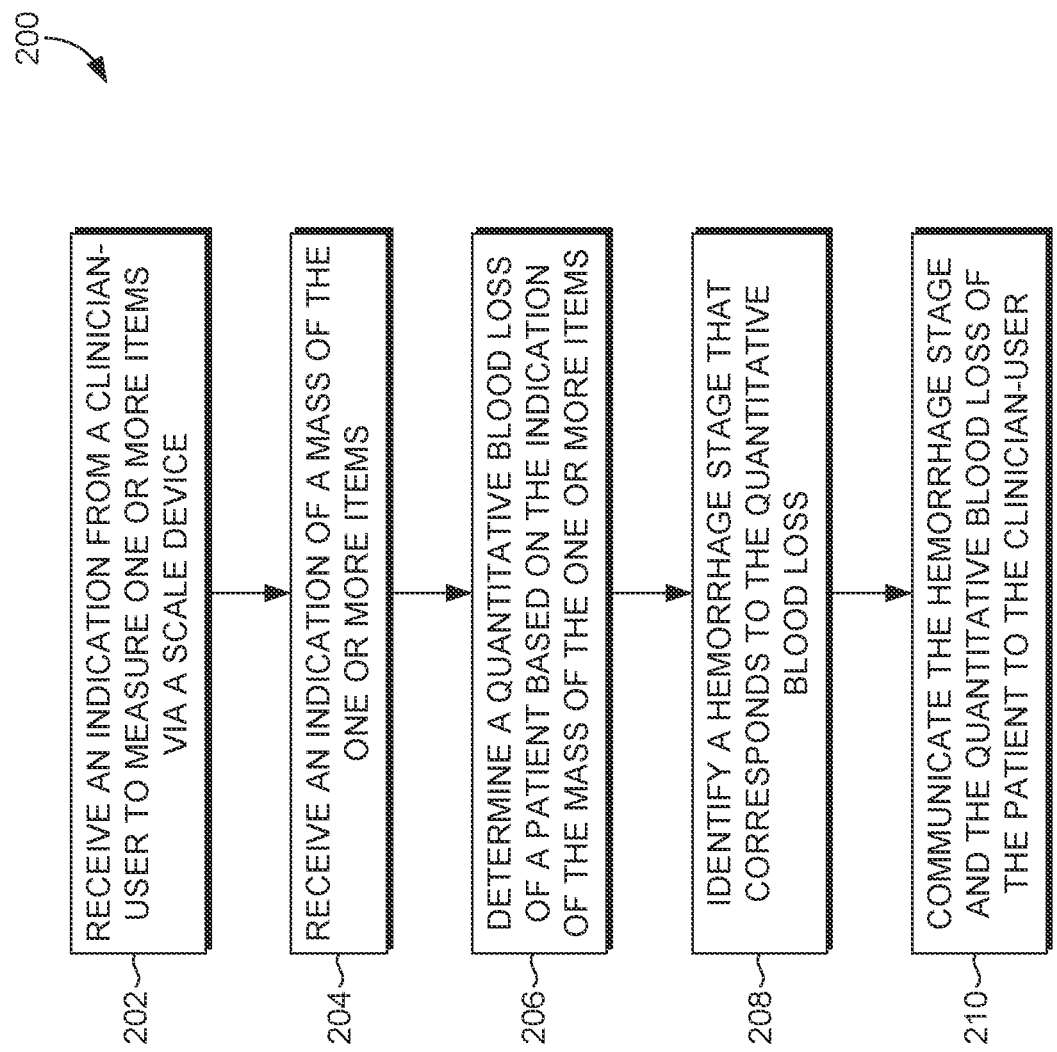
FIG. 2 is a block diagram of an exemplary method for assessing postpartum hemorrhage in accordance with an embodiment of the present invention.

Turning to FIG. 2, a flow diagram is provided illustrating a method 200 for postpartum hemorrhage risk assessment, in accordance with an embodiment of the present invention. In some embodiments, the method 200 may be performed using one or more computing devices including computer storage media, such as previously described. For example, computer storage media may have computer-usable instructions that, when used by one or more computing devices, cause said computing devices to perform the method 200. And, in embodiments, the method is performed at a computing device coupled to a scale device, such as the exemplary remote computer 108 and scale device 110 illustrated in FIG. 1.

Beginning at block 202, the method 200 includes receiving an indication from a clinician-user to measure one or more items via a scale device. In embodiments, the indication triggers the scale device to measure a mass and/or weight of any items physically placed on the scale, for example. For example, a medical staffer may place one patient gown, two towels, and one "chux" pad, each holding, having captured, absorbed, or being saturated with, blood that the patient has hemorrhaged. Then, in this example, the medical staffer uses a user input component to trigger the scale device to initiate measuring the mass or weight of the patient gown, the two towels, and the one group of 5 chux pads. In further embodiments, the indication includes information regarding at least one item type, and at least one quantity of the at least one item type. For example, the medical staff uses a user input component to enter an item type (e.g., patient gown (size regular), 9×9 inch towel, and set of chux pads) and a quantity for each item type (e.g., one patient gown, one towel, one set of five chux pads). The entry of an item type and item quantity may also serve as the indication that triggers the scale device to measure mass and/or weight of the items. Exemplary items include a towel, a wash cloth, a "chux" pad, a "laps" pad, a peripad, a blanket, a delivery kit (e.g., one blanket, 15 lap pads, and one large chux pad), a drape, a draw sheet, a gown, a warming blanket, an ice pack, and the like. Further, exemplary items may include specific sizes, dimensions, or sets of grouped quantities (e.g., set of 5 lap pads, 15 lap pads, etc.). It will further be understood that some items are accounted for without physical placement on the scale. In one example, an intrauterine balloon or balloon tamponade is "weighed" or otherwise accounted for based on user input to the scale and/or the computing device, for example. In some embodiments, a volume of an item may be measured. For example, a balloon tamponade may be measured to reflect a predetermined volume of 500 mL, wherein a balloon tamponade is generally utilized at said volume. In another example, user input may be received that indicates a balloon tamponade is measured as having a volume of 800 mL, as used in the particular hemorrhage event. Accordingly, in some instances, items may be measured based on predetermined volume or mass information and/or a volume may be directly input by a clinician or medical staff (e.g., a user types the volume "800" into the computing device to report the usage volume of the balloon).

In another embodiment, the indication to measure one or more items triggers the scale device to communicate the measurement of the items to a computing device, wherein the scale device automatically measures items as they are placed thereon, but does not send the measurement information to the computing device until the indication is received from user input by the medical staff, for example. In this way, the items are continually measured as the medical staffer places them on the scale, but the measurement information including mass or weight, item type, and quantity are not communicated to the computing device until a user input instructing the scale device to do so is received. It will be understood by those in the art that the indication received from a clinician-user to measure one or more items is not to be considered as limiting the scale to an exact moment of initiating measurement, but rather, may trigger the scale to bundle the measurement information for communicating to a computing device for the purposes of determining a quantitative blood loss and/or hemorrhage stage of a patient.

Continuing to block 204, the method 200 includes receiving an indication of a weight of the one or more items measured. As used herein, the term weight is used herein to refer to mass units (i.e., mL, L, g, kG) as well as weight units, as is quite common in the art. Thus, albeit mass and weight are differentiable scientifically, oftentimes the weight of an object is actually described in mass units, or mass of an object is described in terms of weight units, for ease.

In embodiments, the indication is provided by a scale device to a computing device. In one embodiment, the scale is coupled to a network (e.g., hardwired or wireless, or a combination thereof) over which it communicates with a computing device. In another embodiment, the scale is a separate device that is communicatively coupled to a computing device. And, in yet another embodiment, the scale is integrated with the computing device itself. The scale is physically located at or near the patient bedside during labor and delivery, or is brought to the room of the patient postpartum at the onset of a hemorrhage event. In this way, the scale is easily accessible by medical staff and/or the clinician to place used items thereon.

Generally, the indication to measure items includes one or more of the following: a total weight of all the used items, a previously known individual dry weight for each of the used items, a predefined or predetermined dry weight that corresponds to each of the used items, a total dry weight that corresponds to the sum dry weight of all the used items, an item type for each item, an item type for each of the used items, and a quantity for each item type. In further embodiments, the indication may include additional information such as a patient's weight, age, and the like. As used herein, "dry weight" refers to an item in an unused state (i.e., no blood contact or absorption), removed from any packaging. The dry weight of items may be stored in a memory at the computing device, or stored remotely at a server and/or in a data store. And, the method 200 may include receiving additional indications, in some embodiments. Additional indications might include user input that specifies a type of blood product and quantity as administered to a patient, and/or a medication name and dosage as administered to a patient, for example.

At block 206, the method 200 includes determining a quantitative blood loss of a patient based on the indication of the weight of the one or more items. The quantitative blood loss is the amount of blood lost by the patient. Generally, the quantitative blood loss is defined as the weight of the one or more used items (e.g., towels and chux pads containing blood and blood material of the patient) measured by the scale less the dry weight(s) of each of the used items placed on the scale, in some embodiments. As previously explained, approximately one milliliter (mL) of human blood has a corresponding mass of one gram. Therefore, each gram of difference between the known dry weight of items and the measured weight of the used items corresponds to 1 mL of human blood. As will be understood, a quantitative blood loss may be determined based on the indication of the weight of any used items.

In further embodiments, the quantitative blood loss is determined based on user input that indicates one or more of the following: that a blood product has been administered to the patient prior to the hemorrhage event; that a blood product has been administered to the patient during the hemorrhage event; that a medication or therapeutic agent that affects or may affect blood characteristics (e.g., clotting) has been administered to the patient before and/or during the hemorrhage event; that a medication or therapeutic agent that affects or may affect uterine contractions has been administered to the patient before and/or during the hemorrhage event; etc. Exemplary blood products include units of blood, packed red blood cells, plasma, and platelets. Exemplary medications include oxytocin, methylergonovine (i.e., methergine), misoprostol (i.e., cytotec), 15-methyl prostaglandin (i.e., hemabate), or other pharmaceutical agents.

Exemplary therapeutic agents that affect blood characteristics may include intravenous saline solution, or agents that increase or reduce blood volume or blood composition. The exemplary blood products, medications, and therapeutic agents included herein should not be construed to be a limiting list, but rather, are exemplary in nature and are not limiting. And further, other blood products, medications, and therapeutic agents that are not considered to have any effect on blood characteristics or uterine contractions may be documented during a hemorrhage event in order to analyze the data (e.g., subsequently or in near real time) to identify any positive or negative correlations between said blood products, medications, and therapeutic agents and patient outcome.

And, at block 208, the method 200 includes identifying a hemorrhage stage that corresponds to the quantitative blood loss of the patient. Generally, a hemorrhage stage refers to a predetermined blood loss amount or a predefined blood loss amount to which a postpartum hemorrhage may be found to correspond. It will be understood that a person having skill in the art, generally, that postpartum hemorrhage stages for a vaginal birth are different than the postpartum hemorrhage stages for a cesarean section birth. However, the exemplary guidance, ranges, amounts, and levels discussed herein are not to be construed as finite or limiting, as it will be understood that the criteria defining each hemorrhage stage may be subsequently modified or redefined as determined by agencies and organizations governing the field.

When identifying the hemorrhage stage, the method 200 utilizes the quantitative blood loss determined, one or more vital signs of the patient, one or more lab results (if present), user input, medical interventions employed (e.g., administration of packed red blood cells), and other information or physiological information. For example, the method 200 may utilize the quantitative blood loss, a patient's blood pressure, a heart rate, hemocrit (i.e., a ratio of the volume of red blood cells to the total volume of blood), a platelet count, fibrinogen, other blood proteins, a user input specifying that oxytocin was administered to the patient, an indication of uterotonic usage, a user input identifying one unit of packed red blood cells is being administered, and any other relevant information at or near the time of hemorrhage assessment. As such, in some embodiments, user input may be used to inform a system determining quantitative blood loss and/or a hemorrhage stage of interventions undertaken that may affect said determinations.

In identifying a postpartum hemorrhage stage for a patient having a vaginal delivery, the method 200 may reference data stored (e.g., locally or remotely) that defines hemorrhage stages specific to vaginal deliveries. Each hemorrhage stage may include a predetermined quantitative blood loss range. For example, regarding a postpartum hemorrhage coinciding with a vaginal delivery, a quantitative blood loss between 0 mL and less than or equal to 500 mL defines a Stage 0 postpartum hemorrhage; a quantitative blood loss greater than 500 mL and less than or equal to 1000 mL (i.e., 1 L) defines a Stage 1 postpartum hemorrhage; a quantitative blood loss greater than 1000 mL and less than or equal to 1500 mL defines a Stage 2 postpartum hemorrhage; and a quantitative blood loss greater than 1500 mL defines a Stage 3 postpartum hemorrhage. As defined, it will be understood that these quantitative blood loss ranges define a hemorrhage stage in the absence of abnormal vital signs and/or the absence of irregular lab values. It will also be understood that a hemorrhage stage may also be defined and determined based on other values, ranges, or physiological factors such as: a patient is exhibiting abnormal vital signs, oliguria, more than two units of packed red blood cells have been administered, a patient required two or more uterotonics, and the like. Generally, when a postpartum hemorrhage reaches a Stage 3 status, a massive transfusion protocol is recommended and/or triggered in the clinical setting.

When identifying a postpartum hemorrhage stage for a patient having a vaginal delivery, the method 200 may also reference data stored (e.g., locally or remotely) that defines specific numeric values or value ranges for one or more vital signs and/or defines changes or change thresholds for one or more vital signs. Exemplary vital signs refer to monitored measurements of a patient's heart rate, blood pressure, respiratory rate, and body temperature, for example. An intelligent logic is employed by the method 200 to identify the hemorrhage stage, based on the quantitative blood loss, vital signs, lab results, and other factors, in various embodiments. For example, regarding a postpartum hemorrhage coinciding with a vaginal delivery, when a patient's heart rate reaches a threshold value indicative of tachycardia (e.g., greater than 110/beats per minute), the patient's respiratory rate increases from 12 to 16 breaths per minute to 24 to 30 breaths per minute, and a quantitative blood loss of 476 mL is determined, a Stage 1 postpartum hemorrhage may be identified. Thus, albeit the quantitative blood loss indicates a Stage 0 postpartum hemorrhage, the patient's changing vital signs are evaluated in such a way that a Stage 2 postpartum hemorrhage is identified. In other words, the vital signs of a patient as well as the quantitative blood loss influence the determination of the hemorrhage stage, in embodiments. For example, when a patient experiences abnormal vital signs in addition to a quantitative blood loss that corresponds to a defined range of a lower hemorrhage stage (e.g., Stage 0), a higher hemorrhage stage may be determined (e.g., Stage 1 or Stage 2) as the abnormal vital signs qualitatively contribute to the seriousness of the hemorrhage.

In identifying a hemorrhage stage for a patient having a cesarean section, the method 200 may reference and use stored data (e.g., locally or remotely) that defines hemorrhage stages specific to cesarean sections. For example, regarding a postpartum hemorrhage coinciding with a cesarean section, a quantitative blood loss between 0 mL and less than or equal to 1000 mL defines a Stage 0 postpartum hemorrhage; a quantitative blood loss greater than 1000 mL defines a Stage 1 postpartum hemorrhage; a quantitative blood loss up to 1500 mL defines a Stage 2 postpartum hemorrhage; and a quantitative blood loss greater than 1500 mL defines Stage 3 postpartum hemorrhage. For example, regarding a postpartum hemorrhage coinciding with a cesarean section, when a lab result for the patient has an abnormal result (e.g., low platelet count), the blood pressure of the patient reached a specific change threshold of (e.g., blood pressure has dropped by a predetermined amount in the last few minutes), and a quantitative blood loss of 937 mL is determined, a Stage 3 postpartum hemorrhage may be identified. In other words, the vital signs and lab results of a patient in addition to the quantitative blood loss affect the determination of the hemorrhage stage, in embodiments.

In embodiments, the determination of a hemorrhage stage and or a quantitative blood loss may automatically trigger an action by a computing device, a server, or the like. For example, upon determining that the patient has entered a Stage 1 postpartum hemorrhage, a communication of the patient's blood type, as accessed in an EMR, may be automatically communicated to a blood bank service (e.g., via a network environment) along with one or more of the determined hemorrhage stage for the patient, the quantitative blood loss, the patient's vital signs, and the like, all without requiring user intervention. Automatically notifying another medical service of relevant information reduces the number of user inputs or user interactions that are needed during the emergency. In another example, upon determining that a (new or updated) quantitative blood loss has been determined, all information of the hemorrhage event may be saved or stored as a data file in an EMR and/or an EHR without requiring user input or user intervention, such that a complete record of the hemorrhage event is maintained.

Continuing, the method 200 includes communicating the hemorrhage stage and the quantitative blood loss of the patient to the clinician-user, as shown at block 210. Generally, the hemorrhage stage and the quantitative blood loss are presented to a user on a display device, although other communications of this information are considered to be within the scope of the invention. In alternative embodiments, only one of a hemorrhage stage or a quantitative blood loss of the patient is communicated to the clinician-user. In some embodiments, the hemorrhage stage and/or the quantitative blood loss are communicated to medical personnel outside of the patient's room. For example, the hemorrhage stage and/or the quantitative blood loss may be automatically communicated to a blood bank, an anesthesiologist, and/or a hemorrhage team. The hemorrhage stage and/or the quantitative blood loss may be communicated to another remote computing device, so that the information is viewable or accessible by another clinician, in another example. In further embodiments, a record or log of each and every communication is stored in a database and/or the patient's EMR.

In further embodiments, the method 200 communicates one or more recommendations to the clinician-user. Generally, the recommendations are specific to the postpartum hemorrhage stage that has been identified. Accordingly, the recommendations provided for a Stage 0 postpartum hemorrhage are generally different than the recommendations provided for a Stage 2 postpartum hemorrhage. In embodiments, each of the one or more recommendations are responsive to the specific hemorrhage stage, the quantitative blood loss determined, one or more vital signs and changes thereof, a patient's medical history, and/or one or more lab results, if present. Exemplary recommendations include directives and instructions for a clinician and medical staff to perform specific medical interventions, place medical orders, record information and events during the hemorrhage, report information to other medical staff or another clinician, and/or to evaluate performing an action. For example, a recommendation may specify for a medical staff or clinician to: "consider cause: TONE, TRAUMA, TISSUE, or THROMBIN TONE;" "perform bimanual uterine massage;" "oxytocin IV increase rate;" "empty patient's bladder;" "inspect placenta, vagina, cervix, and uterine cavity;" "call for RN assistance;" and others. In embodiments, multiple recommendations are provided to each of the one or more clinicians and medical staff during a hemorrhage event.

In embodiments, each recommendation may be specific to a healthcare role. For instance, a recommendation may be directed to a nurse role such that a nurse is instructed to perform a recommended action. In another example, a recommendation may be directed to a physician such that the physician is directed to perform a recommended action. In yet another example, a recommendation may be specifically made to a primary registered nurse, wherein the recommendation directs the primary registered nurse to perform a fundal massage. In this way, each particular recommendation may be directed to specific types of clinicians or medical staff, aiding in the delegation of intervention tasks during a hemorrhage event.

In further embodiments, the recommendations may be actionable. An actionable recommendation refers to a recommendation wherein a clinician or medical staff may indicate whether or not the recommended action was performed, was not performed, is currently being performed, or will be performed, via user input. An actionable recommendation may include an actionable item or may be communicated to a user as an actionable item, as previously described. As such, when one or more recommendations are communicated to a clinician, for example, the clinicians may enter input, via the computing device, that the clinician will perform one task and will disregard another. Based on the entered input, the clinician's indications may be saved or stored to an EMR or EHR, or further, displayed on a user interface with an icon or symbol that indicates whether the user input indicated that the recommendation was performed, was not performed, is currently being performed, or will be performed, as well as an identifier that is specific to the clinician having entered the user input.

In further embodiments, the method 200 includes storing the hemorrhage stage and/or the quantitative blood loss of the patient. The hemorrhage stage and/or quantitative blood loss information may be stored temporarily and/or permanently. In some embodiments, the hemorrhage stage and the quantitative blood loss information are stored permanently in a data store, or further, in a patient's EMR or an EHR. In some embodiments, the hemorrhage stage and the quantitative blood loss information are stored temporarily in a memory (e.g., RAM) at a remote computing device until newer or more up-to-date quantitative blood loss information is received. In such an embodiment, the hemorrhage stage may be changed or updated to reflect the more recent quantitative blood loss information, and when such a change in hemorrhage stage occurs, the modified hemorrhage stage may be stored in a memory. In this way, the most recent information may be 'held' in temporary memory until or unless more up-to-date information is received via the scale, computing device, or user input, for example. It will be understood that temporary memory includes RAM or cache memory, for example, and further, that information stored in temporary memory may subsequently be permanently stored in a medical record, for example, in some embodiments. Additionally or alternatively, each quantitative blood loss measured and each hemorrhage stage determined throughout a hemorrhage event of a patient may be stored permanently to an EMR and/or an EHR. Additional information (e.g., patient's vital signs, items weighed, item types, clinician notes) regarding the hemorrhage stage event may be stored on an on-going basis, in some embodiments. Accordingly, a complete record of the events and the progression of a hemorrhage event are electronically recorded and stored.

In some embodiments, the method 200 further comprises determining subsequent quantitative blood loss measurements of a patient. For instance, after the initial quantitative blood loss is determined, the patient may continue to bleed. Subsequently, the clinician and medical staff working to reduce and stop the hemorrhaging may add new items to the scale, as they are used and become saturated with blood. As used herein, "used items" refers to items deployed and utilized during a hemorrhage event that inadvertently capture blood, that are specifically used to capture blood, that assist with reducing the hemorrhage, that are used to clean up blood, and the like. The clinician and/or medical staff may input the type of item(s) and quantity for each type of item(s) that correspond to the newly used items. Therefore, when the newly used items are added to the scale and measured, an indication of a weight of the one or more new items is received at the computing device coupled to the scale device. In response to receiving the subsequent indication of the weight of the new item(s), the method 200 determines a second quantitative blood loss of the patient. Further, in such an embodiment, the method 200 may update the hemorrhage stage based on the second quantitative blood loss alone. Then, the method 200 communicates the one or more of the second quantitative blood loss and an updated hemorrhage stage (when indicated) to the clinician and/or medical staff.

In one embodiment, the second quantitative blood loss does not include the first quantitative blood loss. In such an embodiment, the second quantitative blood loss is added to the first quantitative blood loss to determine a cumulative quantitative blood loss of the patient that reflects a total blood loss experienced by the patient since delivery and/or hemorrhage. The cumulative quantitative blood loss may be updated throughout the hemorrhage event to reflect newly used items measured by the scale device and any subsequently determined quantitative blood loss calculated therefrom. However, during the hemorrhage event, each distinct quantitative blood loss may also be communicated to a clinician along with the cumulative quantitative blood loss, so that the clinician may see whether the hemorrhaging rate (e.g., the amount of blood lost via the hemorrhage over the period of time that has elapsed since a previous quantitative blood loss was previously measured) appears to be increasing or decreasing over time. This may aid the clinician when making intervention choices and actionable items. For example, an increase in the blood loss rate may indicate that the clinician should trigger a massive transfusion protocol, transport the patient to the operating room, and prepare or proceed with performing a laparotomy. In another example, a decrease in blood loss rate may indicate that the current interventions are successfully stabilizing the patient.

In another embodiment, the second quantitative blood loss automatically includes the first quantitative blood loss. In such an embodiment, the second quantitative blood loss is a cumulative quantitative amount of blood loss that includes the patient's blood loss experienced since the onset of a hemorrhage event. With each subsequently received indication of newly used items that are measured by the scale and/or indicated by user input of item type and quantity, another more up-to-date quantitative blood loss may be calculated that includes each of the previous quantitative blood losses determined during a single hemorrhage event. For example, in a further embodiment, a third quantitative blood loss might be calculated based on subsequently received indications of newly used items measured by the scale, for example. This indication is received after the first quantitative blood loss and the second quantitative blood loss were calculated. In this example, the third quantitative blood loss automatically includes the second quantitative blood loss, which included the first quantitative blood loss. Thus, the third quantitative blood loss reflects the most up-to-date cumulative quantitative blood loss of the patient during the single hemorrhage event.

With each subsequent indication of one or more newly used items physically measured by the scale and described by user input of item type and quantity of each item type, the quantitative blood loss may be modified to reflect the patient's overall blood loss during the hemorrhage event. Thus, the cumulative quantitative blood loss of the patient is monitored and tracked throughout the hemorrhage event without the need for any manual calculation on the part of the clinician and/or medical staff. Similarly, the hemorrhage stage of a patient may be updated (as needed) when a new quantitative blood loss corresponds to a change in the hemorrhage stage.

In further embodiments, the method 200 includes automatically initiating a medical order based on the hemorrhage stage identified from the quantitative blood loss determined. For example, when a hemorrhage Stage 3 is identified, an automatic medical order for a number of blood units corresponding to the patient's blood type may be placed to the blood bank. The illustrative examples provided herein are not meant to be limiting, but rather illustrate the expansive capabilities of the invention. It will be understood that a clinician evaluates the exemplary medical orders described, that the clinician controls final decisions in patient care, and that the clinician approves medical orders placed during a hemorrhage event.

Figure 3:
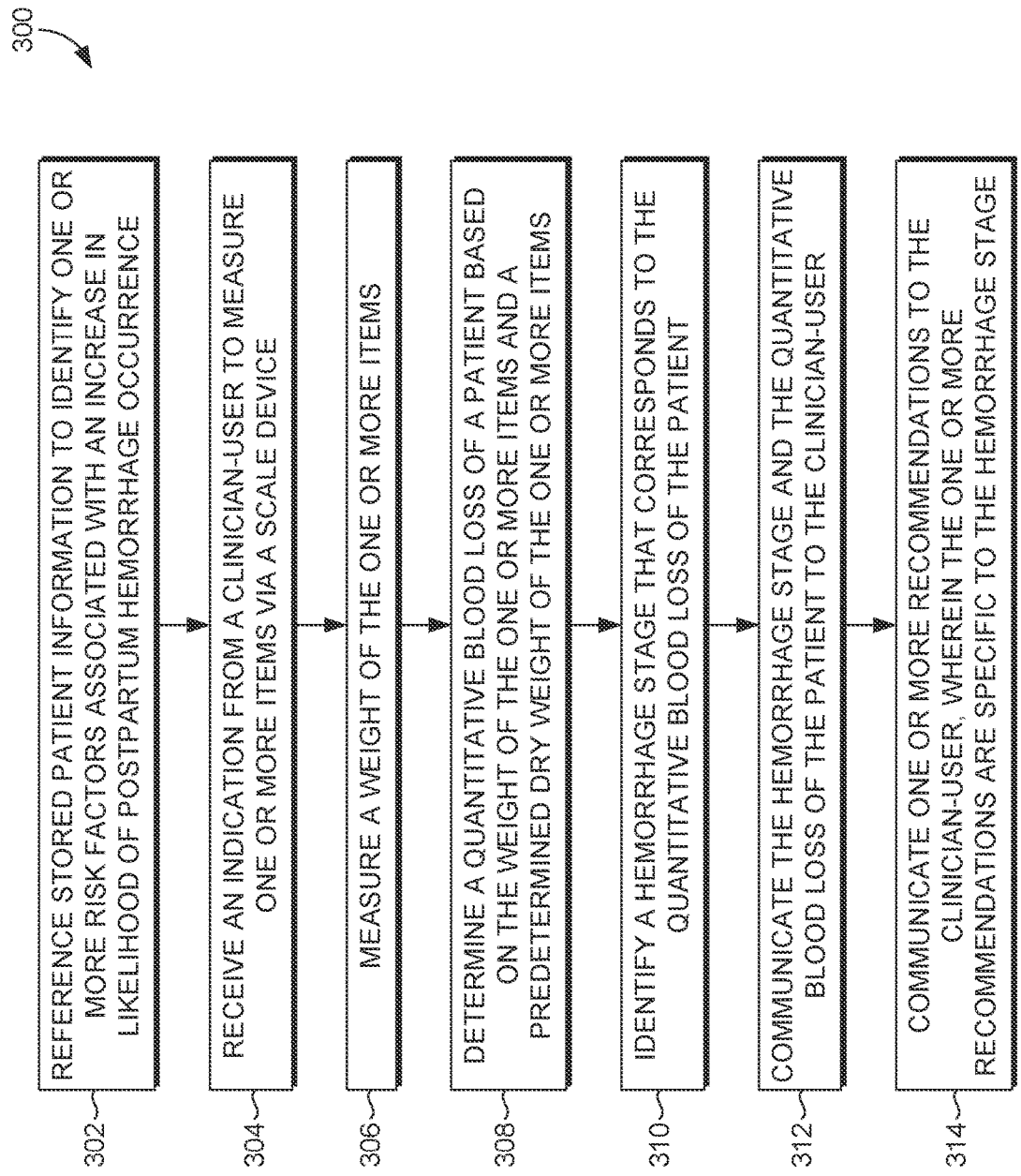
FIG. 3 is a block diagram of an exemplary method for assessing postpartum hemorrhage in accordance with an embodiment of the present invention.

Continuing to FIG. 3, a flow diagram is provided illustrating a method 300 for postpartum hemorrhage risk assessment, in accordance with an embodiment of the present invention. In some embodiments, the method 300 may be performed using one or more computing devices including computer storage media, such as previously described. For example, computer storage media may have computer-usable instructions that, when used by one or more computing devices, cause said computing devices to perform the method 300. And, in embodiments, the method is performed at a computing device coupled to a scale device, such as the exemplary remote computer 108 and scale device 110 illustrated in FIG. 1.

At block 302, the method 300 includes referencing stored patient information to identify one or more risk factors associated with an increase in likelihood of postpartum hemorrhage occurrence. Exemplary patient information includes information stored in an EMR such as a patient's medical history, demographic information, current medical list, and obstetrics history. In embodiments, risk factors may be referenced upon patient admission, intrapartum (occurring during labor and delivery), and/or postpartum.

Generally, one or more risk factors of a patient may be obtained by medical staff or a clinician who interviews the patient directly or reviews the patient's EMR, for example. In some embodiments, postpartum hemorrhage risk factors may be obtained during routine prenatal care visits to an obstetrics doctor's office or upon the patient's admission for labor and delivery. In further embodiments, risk factors, or the lack thereof, may be stored in the patient's electronic medical file, stored (e.g., permanently or temporarily, locally or remotely) in a healthcare management system, and referred to as needed. In other words, a patient may be screened prior to a postpartum hemorrhage event to identify risk factors that may contribute to an increased risk of postpartum hemorrhage. And, in yet another embodiment, risk factors may be referenced postpartum.

Exemplary risk factors include prior uterine incision, prior cesarean section, a multiple pregnancy (i.e., twins, triplets), three or more vaginal deliveries, a known bleeding disorder, a personal history of postpartum hemorrhage, a family history of postpartum hemorrhage, uterine fibroids, induction of labor using oxytocin (previous delivery and/or current labor), chorioamnionitis, estimated fetal weight greater than 4 kG, a body mass index greater than 35, polyhydramnios, suspected placenta accreta or percreta, placenta previa, known coagulopathy, a hemocrit measurement less than 30, and a platelet count less than 100,000/ mm³. It will be understood that these risk factors are illustrative only and should not be construed as limiting. Other risk factors not listed herein for brevity are considered to be within the scope of the invention.

In further embodiments, when at least one risk factor is identified, the method 300 includes using the one or more risk factors associated with an increase in likelihood of postpartum hemorrhage occurrence that are identified to determine a postpartum risk level for the patient. Exemplary risk levels include low, medium, high, a numerical range or scale (e.g., 1 to 100, 1 to 5), a color coding system, or other indicator that signals to a risk level to a clinician or medical staff. In embodiments where at least one risk factor is identified, the method 300 may provide one or more anticipatory recommendations to a clinician or medical staff. The anticipatory recommendation(s) may include an action or intervention that the clinician or medical staff may perform prior to the occurrence of a postpartum hemorrhage in an effort to lower the likelihood of occurrence of a hemorrhage, to reduce negative patient outcomes should a postpartum hemorrhage occur, to notify appropriate personnel (e.g., members of a hemorrhage team, an anesthesia service, a blood bank, and operating room technicians) to be ready and prepare for a potential postpartum hemorrhage for the patient, and/or to prepare the labor and delivery room with hemorrhage-specific supplies needed in case of a postpartum hemorrhage, for example. In other words, an anticipatory recommendation is a recommendation to take an action or perform a task prior to the postpartum phase of labor and delivery. An anticipatory recommendation may be preventative in nature, in embodiments.

In embodiments, anticipatory recommendations may be provided to a clinician or medical staff upon a patient's admission for labor and delivery. As such, a medical staff member may be notified of a particular patient's postpartum hemorrhage risk level and may receive a recommendation to transport a hemorrhage cart to the patient's room at the onset of labor and delivery, for example. In such an example, a hemorrhage cart might include normal saline, blood tubing, rapid transfusion tubing, 18 gauge catheters, 16 gauge catheters, lab draw equipment, blood bank bands, IV pressure bags, lap sponge packs, packing, a manual blood pressure cuff, a balloon tamponade, and a bright task light. In another example, an anesthesia physician might receive an automatic or manually triggered notification (e.g., phone call, text, email, and page) that a patient having a high hemorrhage risk has been admitted to labor and delivery, and therefore, the physician is aware s/he might be called to the patient's room to administer anesthesia and prepare the patient for surgery if needed. Anticipatory recommendations may be specific to a person's role as a physician, surgeon, specialist, primary nurse, a registered nurse, a medical assistant, a midwife, a blood bank team member, and other roles, in further embodiments. As such, anticipatory actions may be undertaken on an as-needed basis prior to occurrence of a postpartum hemorrhage. Then, when a postpartum hemorrhage occurs, the method 300 may proceed with assessment of the hemorrhage as described hereinafter.

The method 300 continues with the receipt of an indication from a clinician-user to measure one or more items via a scale device, at block 304. In embodiments, the indication may include a clinician or medical staff's interaction with the scale and/or computing device via a user interface or user input component. For example, a clinician might use a touchscreen, keyboard, stylus, or mouse to select an option displayed on a graphical user interface, to click a button, or toggle a switch in order to indicate that the clinician seeks to measure or weigh used items using the scale. In another example, the indication might be triggered by the clinician beginning to position used items on the scale, to which the scale automatically detects the change in weight and begins to weigh the items. In yet another example, a clinician might use voice commands to interact with the computing device and/or the scale such that a specific vocal command is an indication to measure one or more items. And, in another example, a medical staffer may click (e.g., with a mouse) a symbol or icon presented on a display, wherein the click indicates the clinician-user seeks to measure used items via the scale in order to assess a hemorrhage event using quantitative blood loss.

At block 306, the method 300 includes measuring a weight of the one or more items. As previously described herein with reference to FIG. 2, a clinician or medical staff places one or more used items on a scale for measuring mass or weight, as used. Some used items may be measured by volume, in embodiments, also previously described hereinabove. Then, at block 308, the method 300 determines a quantitative blood loss of a patient based on the weight of the one or more items, as used, and a predetermined dry weight of the one or more items.

Continuing, at block 310, the method identifies a hemorrhage stage that corresponds to the quantitative blood loss of the patient. As previously explained with regard to the method 200 of FIG. 2, a hemorrhage stage may be identified using quantitative blood loss, vital signs, a patient's medical history, and/or lab results, in some embodiments. Additionally, a patient's medical history and/or EMR may also be referenced and used when identifying a hemorrhage stage. For example, the stored patient information referenced at block 302 of FIG. 3 may further be used at block 310 when identifying the hemorrhage stage. In this way, one or more risk factors of the patient may be analyzed, weighted, or otherwise considered when the hemorrhage stage is identified at block 310.

At block 312, the method 300 includes communicating the hemorrhage stage and the quantitative blood loss of the patient to the clinician-user. In some embodiments, the communication is automatically provided upon identifying the hemorrhage stage. In another embodiment, the communication is provided in response to a computerized indication or a user request. In some embodiments, the quantitative blood loss may be communicated prior to the hemorrhage stage, and vice versa. In another embodiment, the hemorrhage stage and the quantitative blood loss of the patient are communicated together, in real time or near real time. The hemorrhage stage and the quantitative blood loss of the patient may be displayed on a user interface for the clinician-user. Finally, at block 314, the method includes communicating one or more recommendations to the clinician-user, wherein the one or more recommendations are specific to the hemorrhage stage.

FIGS. 4-14 provide GUIs of exemplary for assessing postpartum hemorrhage in accordance with an embodiment of the present invention. In embodiments, a clinician-user or medical staff user may use the GUIs of FIGS. 4-14 to interact with and implement the methods 200 and 300 of FIGS. 2 and 3.

Figure 4:
FIG. 4 is an exemplary graphical user interface (GUI) for assessing postpartum hemorrhage in accordance with an embodiment of the present invention.

At FIG. 4, the exemplary GUI 400 provides for a "Postpartum Hemorrhage Advisor." The GUI 400 includes an indication of a patient's risk level 402, an indication of current hemorrhage stage 404, individual indicators 406, 408, and 410 for each of the patient's vital signs 405, and selectable tabs 412 and 414 that may be selected with user input to toggle a user between a Risk Assessment information and Stage and Recommendations information. The GUI 400 further includes one or more actionable recommendations 416, organized by role, such as "Primary Nurse" 418, "Physician" 420, and "Blood Bank" 422. In GUI 400, the actionable recommendations 416 are anticipatory recommendations and/or are specific to a Stage 0 postpartum hemorrhage. For example, an anticipatory recommendation to "Perform the appropriate anticipatory interventions" and "active $3^{rd}$ stage management" is shown as directed to the role of Physician. It will generally be understood in the art that "$3^{rd}$ stage" refers to the third stage of labor and delivery wherein the infant has been fully delivered through completed delivery of the placenta.

Figure 5:
FIG. 5 is an exemplary GUI for assessing postpartum hemorrhage in accordance with an embodiment of the present invention.

As shown in FIG. 4, an arrow 424 corresponds to user input via a mouse, for example, wherein the user is seeking to launch or open a quantitative blood loss function of the Postpartum Hemorrhage Advisor. The user may launch this quantitative blood loss function to weigh more used items. As shown, the patient currently has a quantitative blood loss of 436.00 mL. By using the arrow 424 to click, hover, or otherwise select an illustrative "+" icon, the quantitative blood loss functionality may be opened, as shown in FIG. 5. Notably, the user is not redirected to a new GUI or a new window, but rather, the quantitative blood loss functionality section 500 appears on the same screen as a new section that visually shifts the selectable tabs 412 and 414 of Risk Assessment information and Stage and Recommendations information downward. The section includes a summary section 430 wherein a total weight of all the used items may be displayed alongside the total dry weight corresponding to the item, if unused, and further, a subtotal weight may be displayed. Additionally, the summary section 430 includes an area 432 for displaying an updated or new quantitative blood loss and an area 434 for displaying a previously determined total weight.

In the quantitative blood loss functionality section 500, several different items are presented with identifiable item types and selectable quantities for quick and easy selection by a user. The item types may also be listed with mass information. Exemplary identifiable item types with masses are presented including Towel (50 gr), Chux (25 gr), Delivery Kit (150 gr), and Pad-5x (50 gr). In embodiments, one or more open field boxes 426 and 428 are available for directly receiving user input. For example, open field box 428 corresponds to a balloon item for which a volume may be entered. And, open field box 426 corresponds to a field for receiving direct user input of the mass or weight of the scale device. As such, a user may enter items and the quantity thereof into the quantitative blood loss functionality section 500. Generally, the items entered and the corresponding quantity of each item type entered by the user will reflect actual used items placed on a scale for weighing.

In FIG. 5, several user indications are shown together. The illustrative arrows 424B, 424C, and 424D are meant to indicate how the user relocates the arrow from one location to another, in order to input information. The arrow 424B indicates the user seeks to input information regarding a delivery kit item to be weighed, the arrow 424C indicates the user seeks to input information regarding a pad-10x item to be weighed, and the arrow 424D indicates the user seeks to input information regarding a large blue pad item, for instance.

Figure 6:
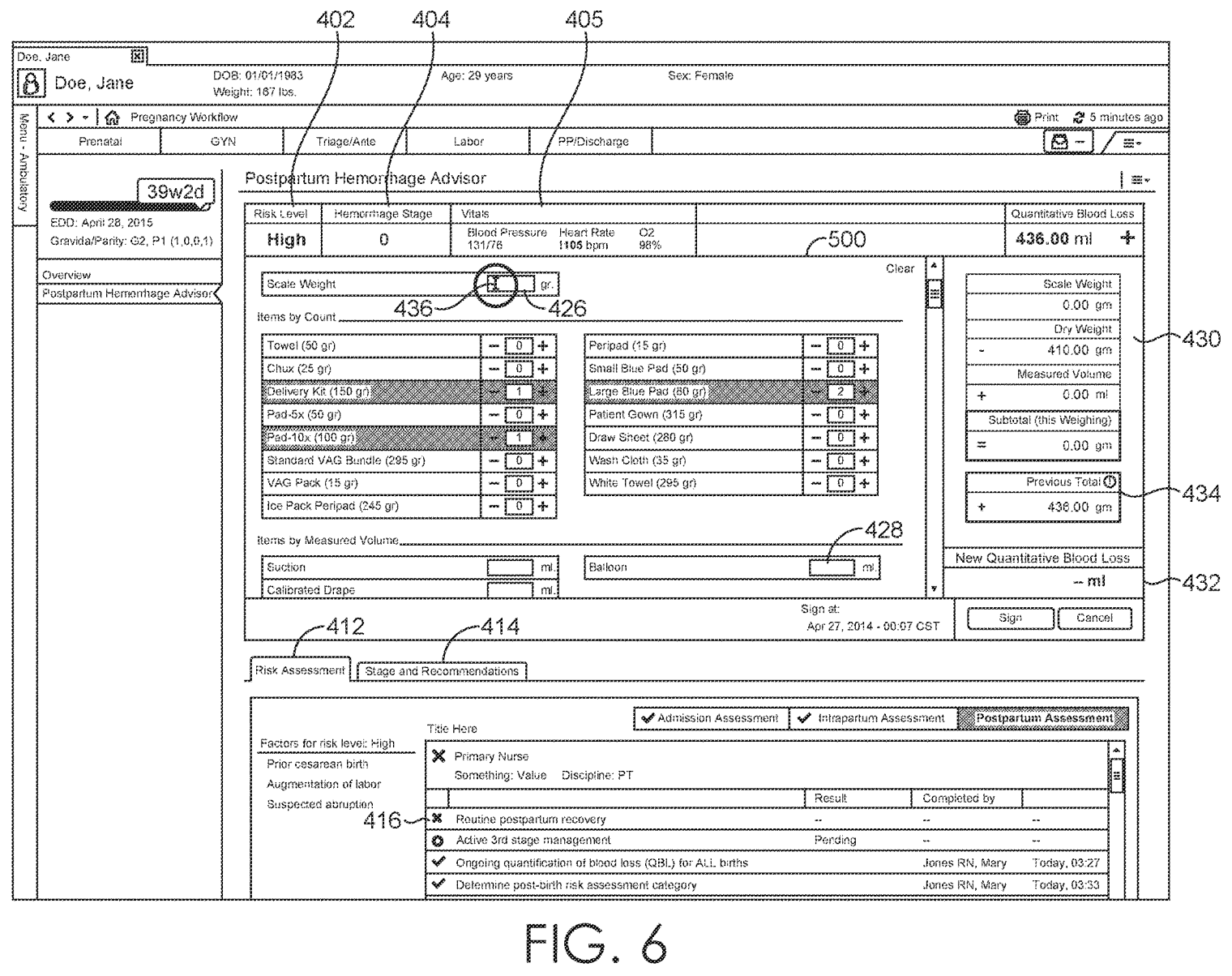

Once entered, the item type and quantities will be displayed, as shown in FIG. 6. The used items entered by the user are shown shaded in dark gray for the purposes of this description only. Additionally, the total dry weight that corresponds to all of the used items indicated by the user input is displayed in the quantitative blood loss functionality section 500 along with the total measurement of previously entered or previously indicated items. In FIG. 6, a cursor 436 indicates the user has moved the arrow to the open field box 426 in order to directly enter information that in this instance corresponds to the weight of the scale. In some instances, the weight of the scale is included in the quantitative blood loss assessment. The weight of the scale is included in order to provide a complete record of all the items weighed and accounted for, for each measurement performed. The weight of the scale can further be used to evaluate calibration of the scale, evaluate the accuracy of calculations, and control the quality of determinations made using the Postpartum Hemorrhage Advisor. After entering the weight of the scale, the open field box 426 reflects the weight of the scale, as entered by a user (e.g., 707.25 grams). Additionally, the quantitative blood loss functionality section 500 now displays the scale's weight alongside the total dry weight of the used items added by user input in FIGS. 5 and 6.

Figure 7:
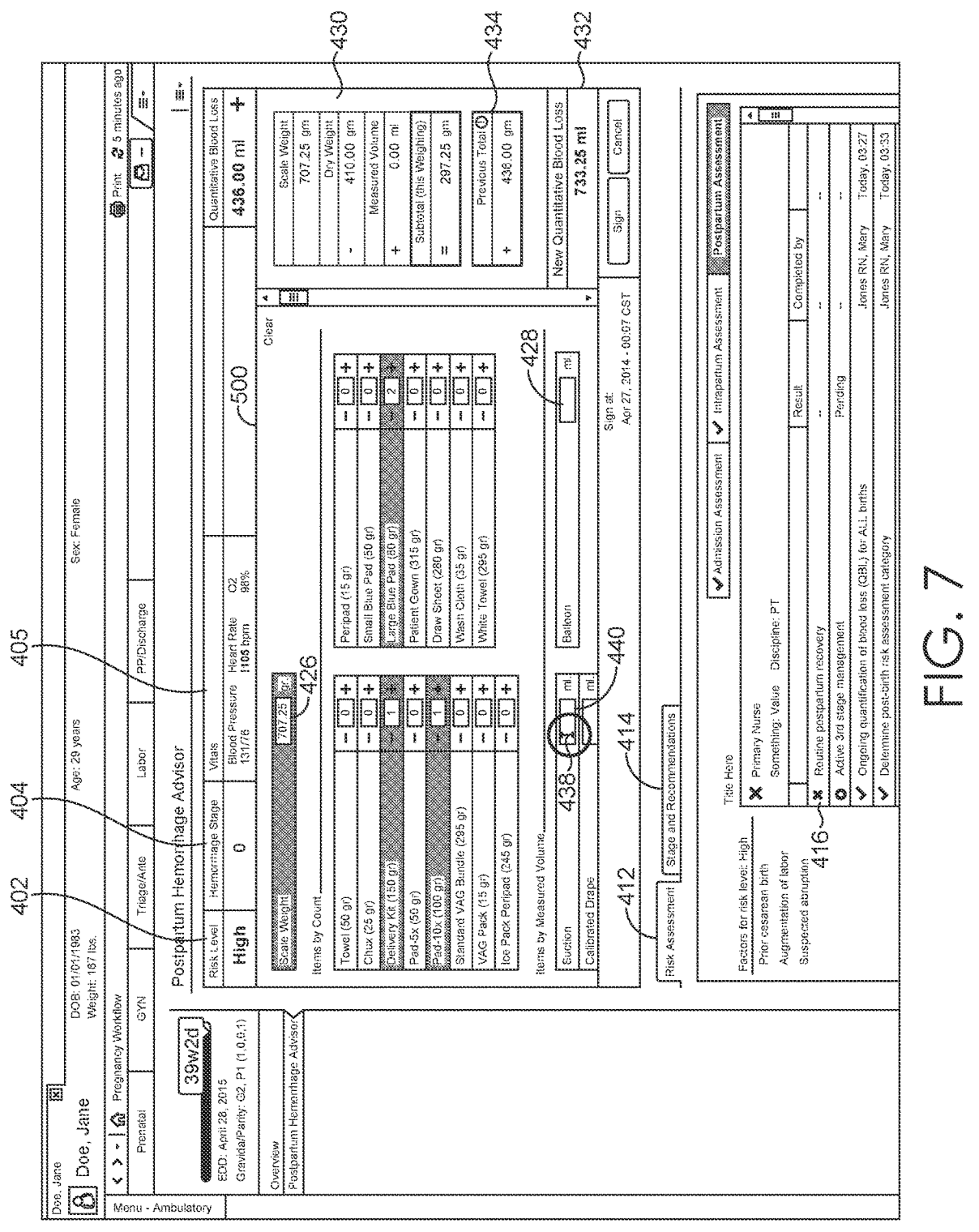
Figure 8:
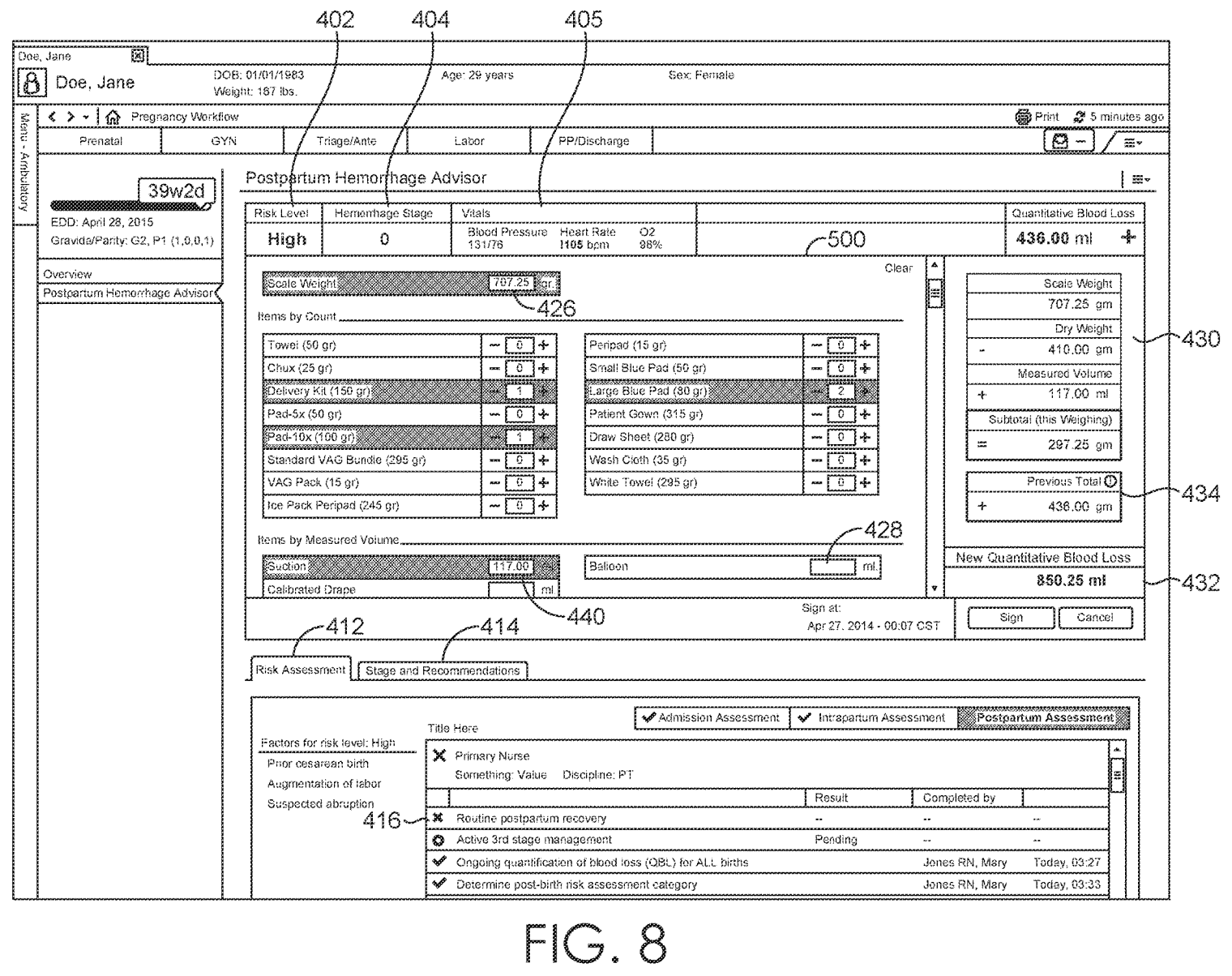

In FIG. 7, the cursor 438 indicates the user has moved the arrow to the open field box 440 in order to directly enter information regarding a volume of a suction (e.g., item type) that is in use during the hemorrhage event. In FIG. 7, at least some items are shown as measurable in volume, rather than grams. As shown in FIG. 8, the user input indicates a volume amount that corresponds to or describes the volume of the suction item and that has been entered into the open field box 440 corresponding to the item type "suction." This indicates that the suction item is in use and the user seeks to 'weigh' the item or otherwise account for it in determining the quantitative blood loss. In FIG. 8, the quantitative blood loss functionality section 500 displays the scale weight, the total dry weight of used items, a measured volume, a subtotal of the scale weight, the total dry weight of used items, and the measured volume. Furthermore, the quantitative blood loss functionality section 500 displays the new quantitative blood loss based on the scale weight, the total dry weight of used items, and the measured volume.

Figure 9:
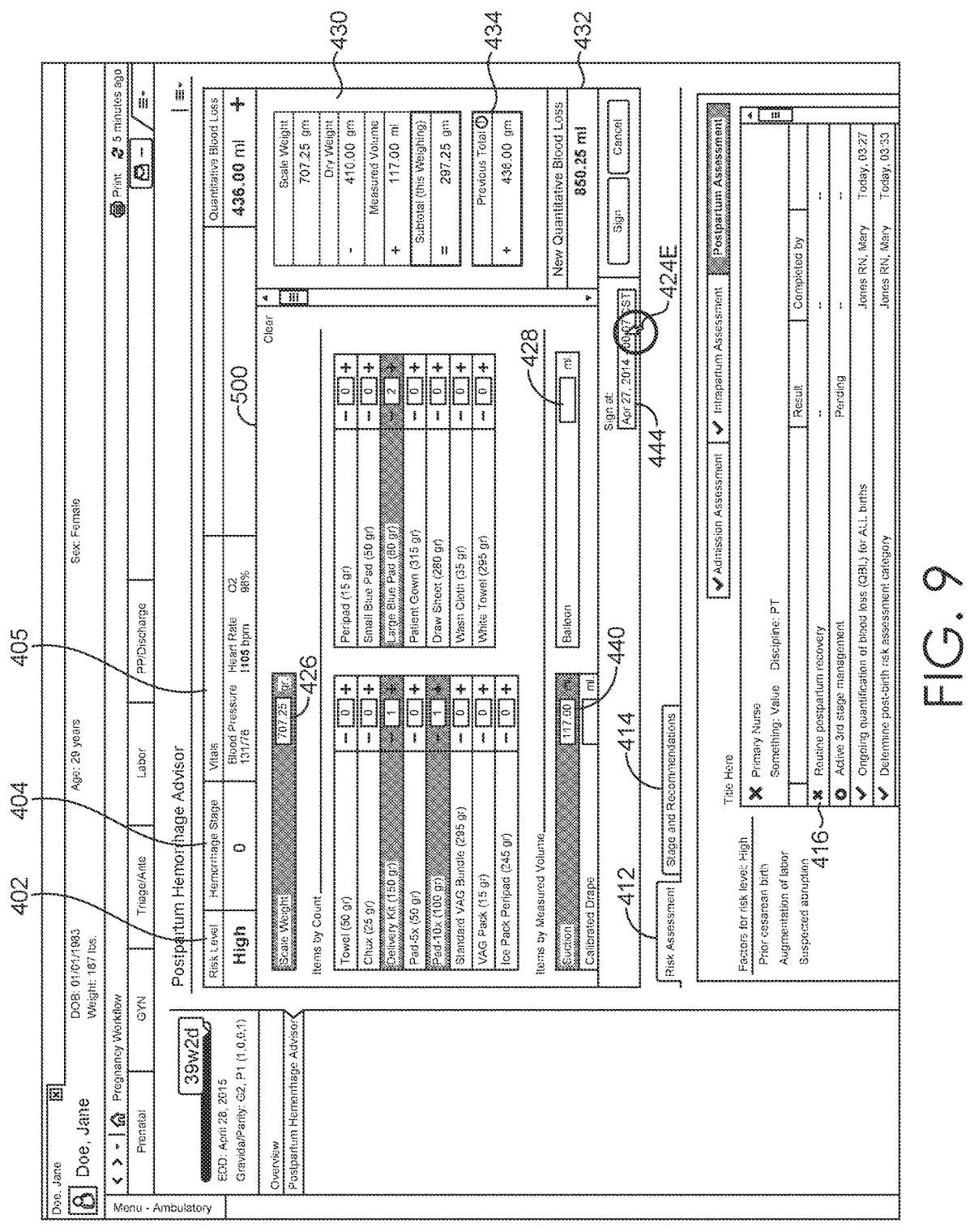
Figure 10:
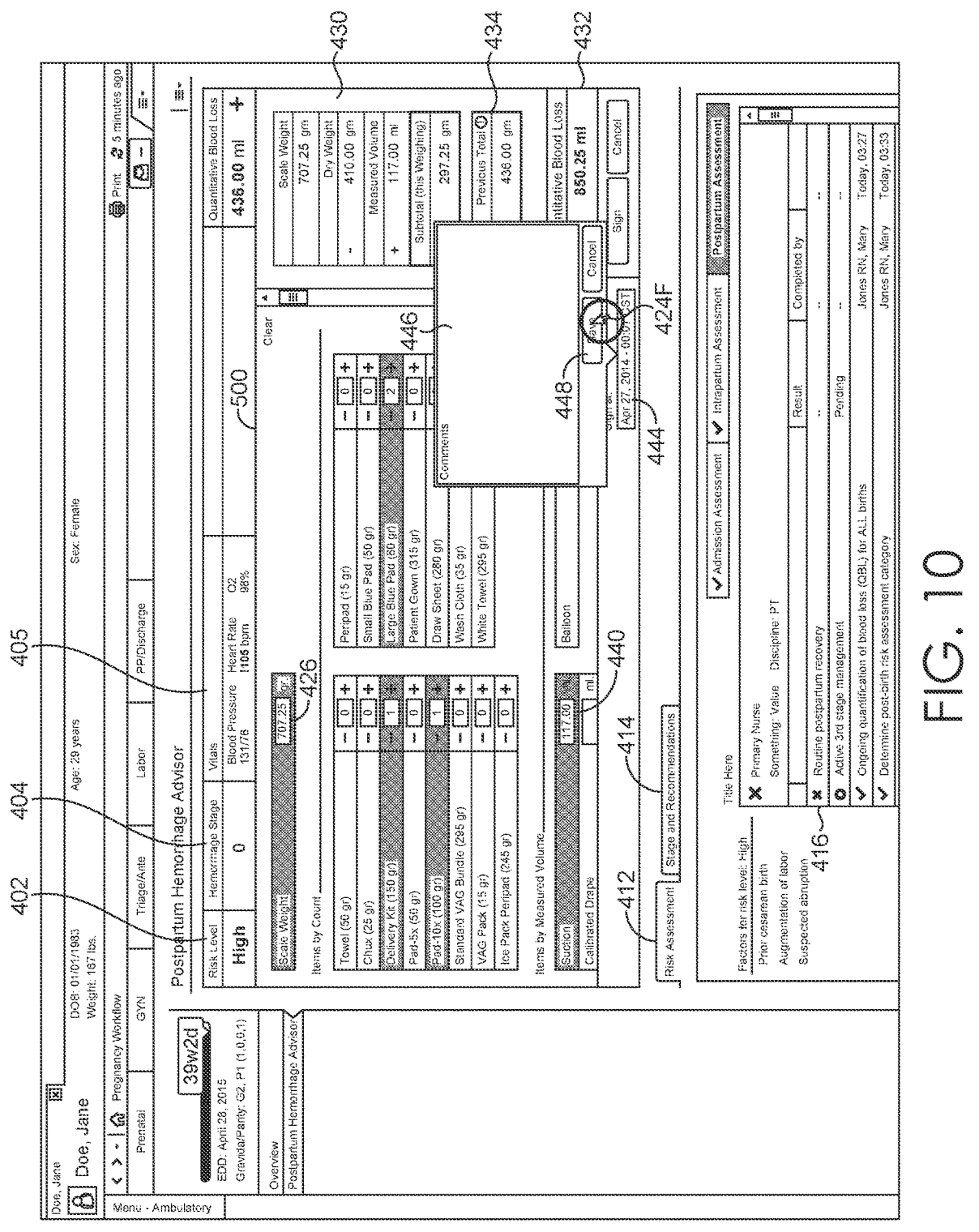

Continuing to FIG. 9, the user has moved the arrow 424E to a time stamp box 444 in order to electronically time-stamp the new quantitative blood loss of the patient. In further embodiments, the information regarding the new quantitative blood loss is recorded to a medical file and/or the patient's EMR. Exemplary information includes the vital signs readings, each used item type and quantities thereof, each item measured by volume and volume quantities entered, the scale weight, the total dry weight of the used items, the measured volume of used items, the subtotal, the previous total, and the like. After selecting to time-stamp the new quantitative blood loss of the patient, the user may enter comments into a pop-up box 446, shown in FIG. 10. Comments generally include relevant information regarding the hemorrhage event. The information entered may then be saved or stored in response to a received user indication, for instance, selection of a "save" button 448 as shown with arrow 424F. The information received may also be stored in an EMR and/or an HER, as a data file, a log file, a subset of files, or the like.

Figure 11:
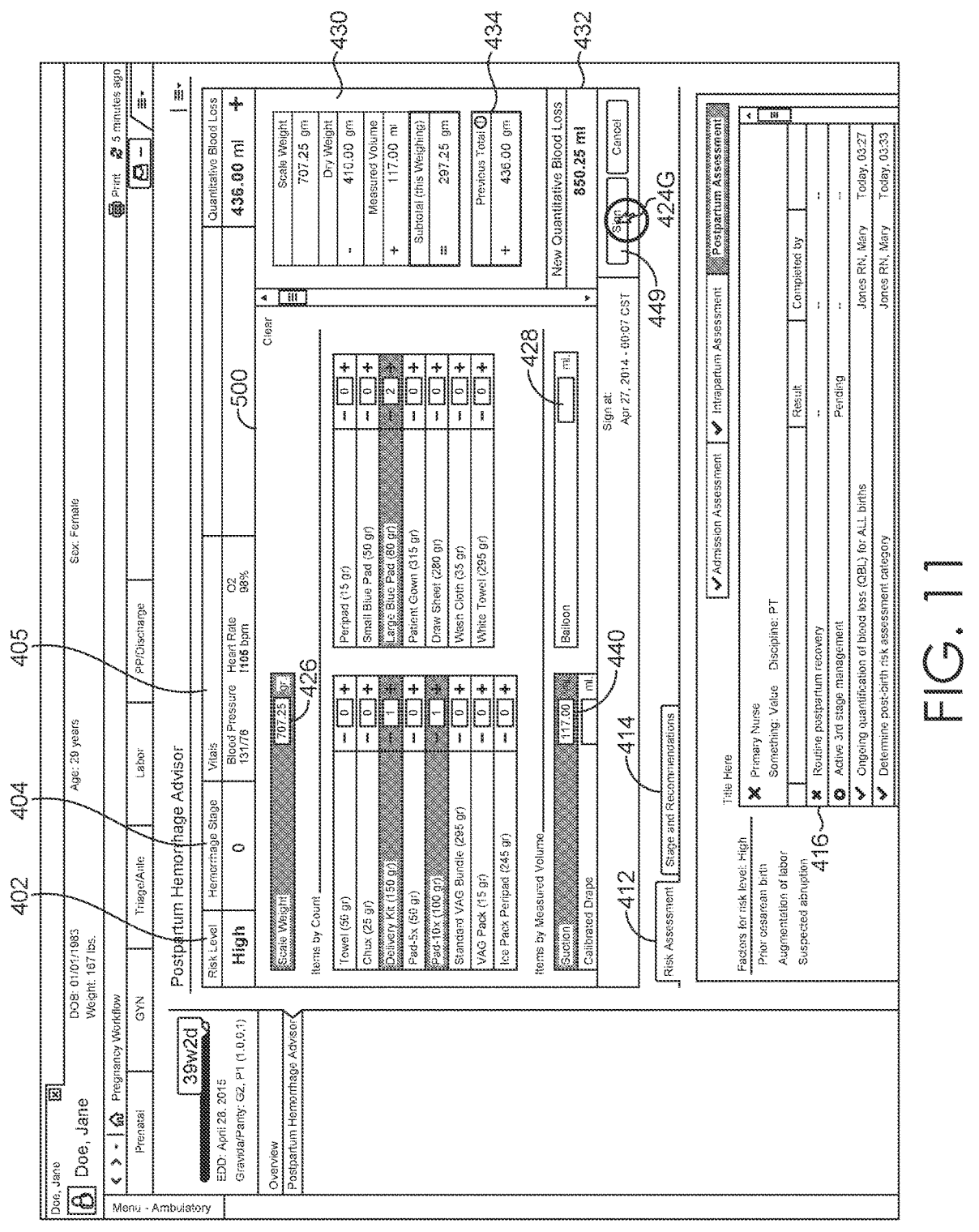
Figure 12:
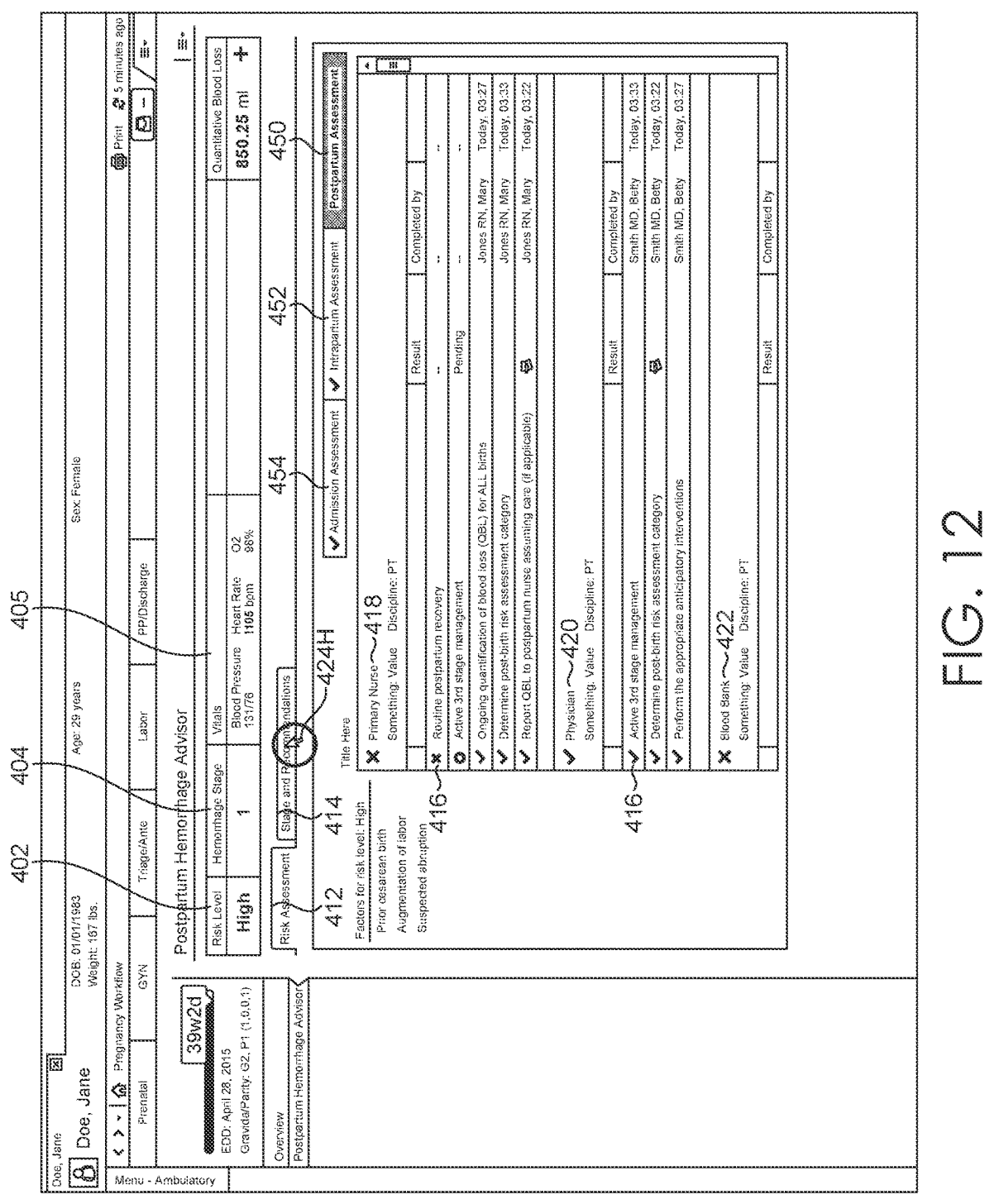

At FIG. 11, the user has moved the arrow 424G to a sign button 449 in order to electronically sign the new quantitative blood loss of the patient. Upon selection of the sign button 449, all hemorrhage event information may be electronically saved or stored, in embodiments. For example, the item types, the quantity of each item type, the patient's vital signs, the previously determined quantitative blood loss, the new quantitative blood loss, and other information may be saved in a data log file or a subset of data file to the patient's EMR and/or an HER, in embodiments. And, as shown in FIG. 12, a cumulative quantitative blood loss for this patient's particular hemorrhage event is displayed (e.g., 850.25 mL), the quantitative blood loss functionality section 500 is automatically hidden, and the selectable tabs 412 and 414 are shifted upwards on the screen to their original location. Additionally, the postpartum hemorrhage has been identified as changing from Stage 0 to Stage 1, such that an indication of the current hemorrhage stage 404 is displayed. In further embodiments, acceptance of an electronic signature may automatically cause one or more actionable items to be performed, such as communicating notification to a blood bank that indicates the cumulative quantitative blood loss, as updated. Such actionable items provide the blood bank with notice that more packed red blood cells may be needed, for example. As previously explained, it will be understood that a clinician evaluates the exemplary medical orders described, that the clinician controls final decisions in patient care, and that the clinician approves medical orders placed during a hemorrhage event, including actionable actions.

Turning to FIG. 12, the user has moved the arrow 424H in order to select the Stage and Recommendations tab 414. As shown, the current recommendations 416 correspond to the Risk Assessment selectable tab 412, during a postpartum assessment indicated by phase box 450. It will be understood that other boxes 452 and 454 may be selected so that a user may view recommendations that are specific to distinct phases of a patient's care for labor delivery. For example, an assessment of a patient's risk for postpartum hemorrhage may be assessed upon the patient's admission (phase box 454) using recommendations that may be performed at the time of admission. In another example, an assessment of a patient's risk for postpartum hemorrhage may be assessed during or throughout labor and delivery (phase box 452) using recommendations that may be performed during that time.

Figure 13:
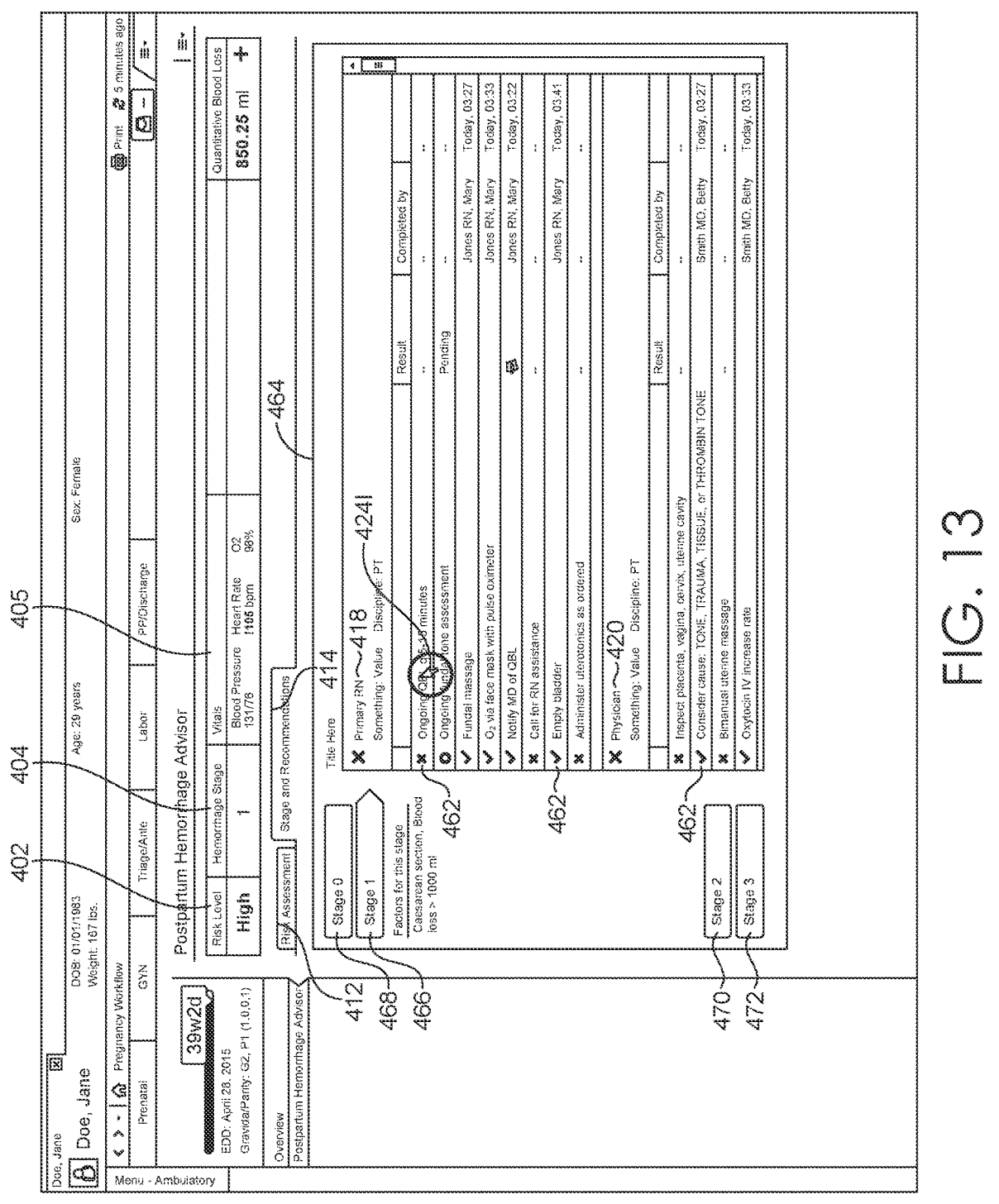

Upon selecting the Stage and Recommendations tab 414, relevant information is displayed on the GUI, as shown in FIG. 13. The Stage and Recommendation section 464 includes recommendations 462 that are relevant to a Stage 1 postpartum hemorrhage. To the left of the Stage and Recommendation section 464 is a Stage 1 bookmark 466, which is visually distinguishable from the other hemorrhage stages, shown as bookmarks 468, 470, and 472. Recommendations that are specific to the other hemorrhage stages, shown as bookmarks 468, 470, and 472, are not displayed because the patient is currently in a different postpartum stage, Stage 1. Recommendations that are specific to the other hemorrhage stages, shown as bookmarks 468, 470, and 472, may be displayed if or when a corresponding or matching hemorrhage stage is identified by the Postpartum Hemorrhage Advisor based at least on the cumulative quantitative blood loss of the patient.

Figure 14:
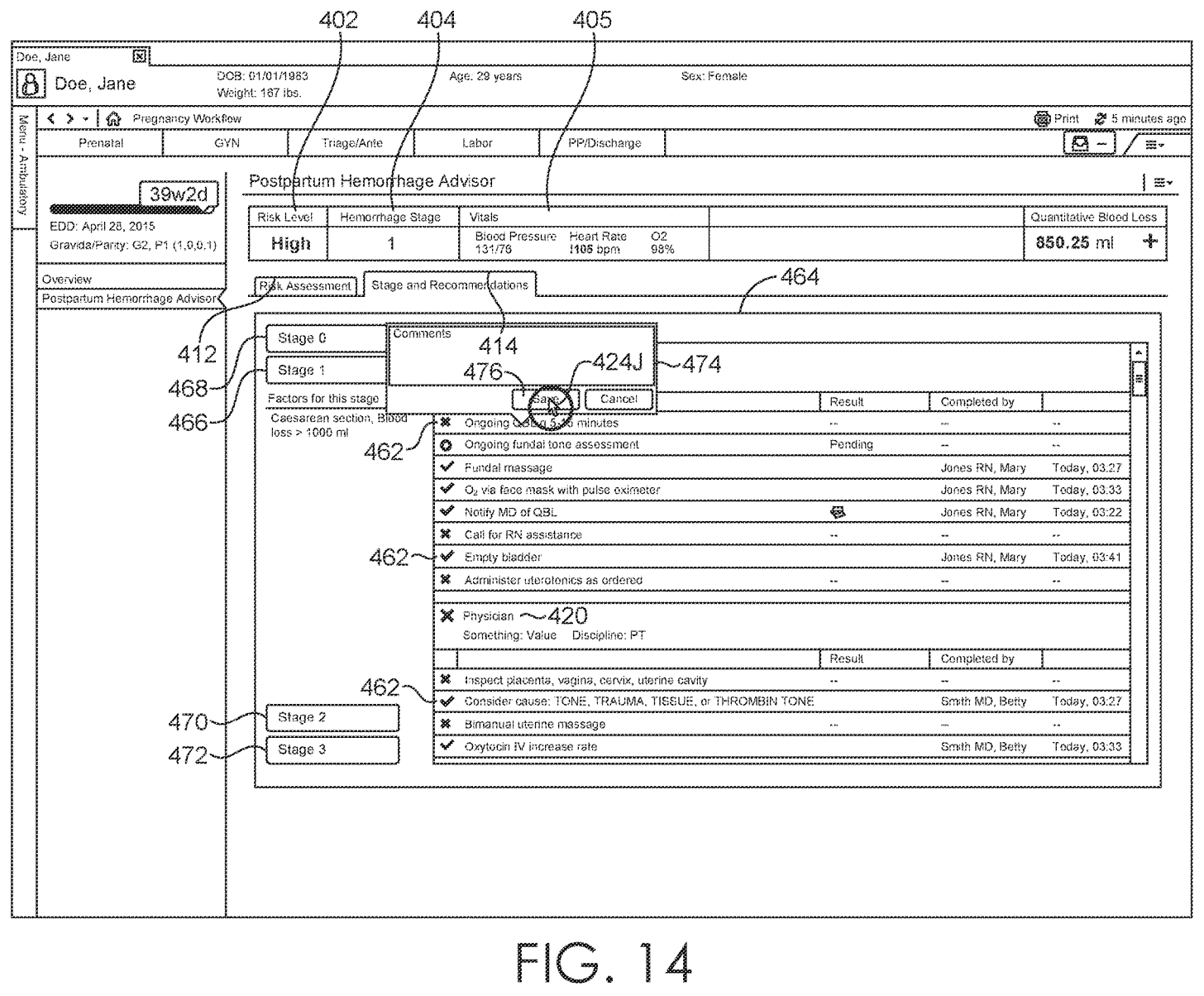

In FIG. 13, the user has moved the arrow 424I in order to select a particular recommendation, shown as "Ongoing QBL q5-15 minutes." Upon receiving an indication of the selection, a pop-up window 474 is displayed, as shown in FIG. 14. A user may input information that is relevant to the particular recommendation "Ongoing QBL q5-15 minutes," and save the information. As illustrated in FIG. 14, the user has relocated the arrow 424J in order to select a "save" button 476 and store any entered information of the pop-up window 474 to an EMR or EHR, in embodiments. In this way, a user may track which recommendations are addressed, not addressed, comments or reasoning for not addressing a recommendation (e.g., pop-up window 474), will be addressed, and the like during each stage of a postpartum hemorrhage.

The recommendations may be based on the most up-to-date clinical guidelines for postpartum hemorrhage, for example. The recommendations may be flanked to the left or right with a symbol or icon that signals to a user whether that corresponding recommendation was performed, was not performed, is currently being performed, or will be performed. Exemplary symbols or icons include an "X," an "O," a checkmark, and the like. For example, it will be generally understood that a checkmark flanking a recommendation indicates that the recommendation has been addressed or otherwise performed. In another example, it will be understood that an "X" placed next to a recommendation indicates that the recommendation has not been addressed or will not be performed. In further embodiments, colors may be used in addition to an icon to signal to a user whether that corresponding recommendation was performed, was not performed, is currently being performed, or will be performed. For instance, the color red may be associated with a recommendation that has not been performed and/or will not be performed, whereas the color green may be associated with a recommendation that has been performed or completed.

The present invention has been described in relation to particular embodiments, which are intended in all respects to be illustrative rather than restrictive. Further, the present invention is not limited to these embodiments, but variations and modifications may be made without departing from the scope of the present invention.

What is claimed is:

1. A method comprising:
causing a scale device that is communicatively coupled to a computing device to measure a total mass of a plurality of items for determining blood loss;
determining, by the computing device, a total unused mass of the plurality of items based on a user-input quantity of each of the plurality of items multiplied by a predefined mass of each corresponding item type of the plurality of items;
determining, by the computing device, a quantitative blood loss of a patient based on the total mass relative to the total unused mass of the plurality of items;
automatically identifying, by the computing device, a hemorrhage stage that corresponds to the quantitative blood loss; and
automatically initiating, by the computing device, a medical order including at least one unit of blood that is specific to the hemorrhage stage identified, wherein the medical order includes a quantity of blood units corresponding to the quantitative blood loss of the patient, wherein the quantity of blood units corresponding to the quantitative blood loss is administered to the patient.

2. The method of claim 1, further comprising automatically communicating the quantitative blood loss and the medical order for storage in an electronic medical record (EMR) that is associated with the patient.

3. The method of claim 1, further comprising, subsequent to initiating the medical order, causing the scale device that is communicatively coupled to the computing device to measure an updated total mass.

4. The method of claim 3, further comprising determining an updated quantitative blood loss of the patient based on the updated total mass.

5. The method of claim 4, further comprising updating the hemorrhage stage based on the updated quantitative blood loss.

6. The method of claim 5, further comprising automatically communicating the updated quantitative blood loss for storage in an electronic medical record (EMR) that is associated with the patient.

7. The method of claim 1, further comprising communicating a notification to a medical service.

8. The method of claim 1, further comprising communicating a notification to a blood bank service using a network, wherein the notification includes a blood type specific to the patient.

9. One or more non-transitory computer storage media having computer-usable instructions that perform a method when executed by one or more processors, the non-transitory computer storage media comprising:
   causing a scale device that is communicatively coupled to a computing device to measure a total mass of a plurality of items for determining blood loss;
   determining, by the computing device, a total unused mass of the plurality of items based on a user-input quantity of each of the plurality of items multiplied by a predefined mass of each corresponding item type of the plurality of items;
   determining, by the computing device, a quantitative blood loss of a patient based on the total mass relative to the total unused mass of the plurality of items;
   automatically identifying, by the computing device, a hemorrhage stage that corresponds to the quantitative blood loss; and
   automatically initiating, by the computing device, a medical order including at least one unit of blood that is specific to the hemorrhage stage identified, wherein the medical order includes a quantity of blood units corresponding to the quantitative blood loss of the patient, wherein the quantity of blood units corresponding to the quantitative blood loss is administered to the patient.

10. The non-transitory computer storage media of claim 9, further comprising receiving an indication of an administration of the quantity of blood units to the patient.

11. The non-transitory computer storage media of claim 10, further comprising determining, by the computing device, an updated quantitative blood loss of the patient based on the total mass relative to the total unused mass and based on the indication.

12. The non-transitory computer storage media of claim 11, further comprising automatically identifying, by the computing device, an updated hemorrhage stage that corresponds to the updated quantitative blood loss.

13. The non-transitory computer storage media of claim 9, further comprising receiving an indication of an administration of a therapeutic agent to the patient that affects blood characteristics.

14. The non-transitory computer storage media of claim 13, further comprising determining, by the computing device, an updated quantitative blood loss of the patient based on the total mass relative to the total unused mass and based on the indication.

15. The non-transitory computer storage media of claim 9, wherein automatically identifying the hemorrhage stage further comprises identifying a vitals measurement of the patient.

16. The non-transitory computer storage media of claim 9, wherein automatically identifying the hemorrhage stage further comprises identifying a risk characteristic of the patient.

17. The non-transitory computer storage media of claim 9, further comprising determining a blood loss rate based on the total mass of the plurality of items measured via the scale device and at least one previously-measured quantitative blood loss of the patient.

18. A system for comprising:
   one or more processors that are communicatively coupled to a scale device, wherein the one or more processors are configured to:
   cause the scale device that is communicatively coupled to a computing device to measure a total mass of a plurality of items for determining blood loss;
   determine a total unused mass of the plurality of items based on a user-input quantity of each of the plurality of items multiplied by a predefined mass of each corresponding item type of the plurality of items;
   determine a quantitative blood loss of a patient based on the total mass relative to the total unused mass of the plurality of items;
   automatically identify a hemorrhage stage that corresponds to the quantitative blood loss; and
   automatically initiate a medical order including at least one unit of blood that is specific to the hemorrhage stage identified, wherein the medical order includes a quantity of blood units corresponding to the quantitative blood loss of the patient, wherein the quantity of blood units corresponding to the quantitative blood loss is administered to the patient.

19. The method according to claim 1, wherein the identified hemorrhage stage is based at least in part on one or more vital signs of the patient, one or more lab results of the patient, or a medical intervention employed.

20. The method according to claim 1, wherein the identified hemorrhage stage is based at least in part on one or more of the quantitative blood loss, a blood pressure of the patient, a heart rate of the patient, a hemocrit of the patient, or a platelet count of the patient.

* * * * *